(12) United States Patent
Che et al.

(10) Patent No.: US 10,800,717 B2
(45) Date of Patent: Oct. 13, 2020

(54) PALLADIUM-BASED SUPPORTED HYDROGENATION CATALYST, AND PREPARATION METHOD AND APPLICATION THEREOF

(71) Applicant: PetroChina Company Limited, Beijing (CN)

(72) Inventors: Chunxia Che, Beijing (CN); Yulong Liang, Beijing (CN); Ying Qian, Beijing (CN); Wei Han, Beijing (CN); Feng Zhang, Beijing (CN); Galian Gou, Beijing (CN); Xilin Jing, Beijing (CN); Xiaoxin Chang, Beijing (CN); Qiang Gui, Beijing (CN); Lifen Gu, Beijing (CN); Wei Xie, Beijing (CN); Zhongdong Zhang, Beijing (CN); Dehua Huang, Beijing (CN); Duping Tan, Beijing (CN); Yuan Gao, Beijing (CN); Lin Cheng, Beijing (CN)

(73) Assignee: PetroChina Company Limited, Beijing (CN)

( * ) Notice: Subject to any disclaimer, the term of this patent is extended or adjusted under 35 U.S.C. 154(b) by 174 days.

(21) Appl. No.: 16/010,005

(22) Filed: Jun. 15, 2018

(65) Prior Publication Data

US 2018/0290949 A1    Oct. 11, 2018

Related U.S. Application Data

(63) Continuation of application No. PCT/CN2016/082976, filed on May 23, 2016.

(51) Int. Cl.
*C07C 5/09*     (2006.01)
*B01J 23/50*    (2006.01)
(Continued)

(52) U.S. Cl.
CPC .......... *C07C 5/09* (2013.01); *B01J 23/50* (2013.01); *B01J 23/52* (2013.01); *B01J 23/628* (2013.01);
(Continued)

(58) Field of Classification Search
CPC ... B01J 23/44; B01J 23/50; B01J 23/52; B01J 23/8926; B01J 37/0203; B01J 37/08;
(Continued)

(56) References Cited

U.S. PATENT DOCUMENTS 3,240,698 A * 3/1966 Leak .................... C07C 4/18
                                                208/143
4,361,499 A * 11/1982 Hargis ............... B01J 23/8906
                                                502/162

(Continued)

FOREIGN PATENT DOCUMENTS

CN    102205243 A    10/2011
CN    102206130 A    10/2011
(Continued)

OTHER PUBLICATIONS

Machine translation of CN102206130, publication date Oct. 5, 2011.*

(Continued)

*Primary Examiner* — Jun Li
(74) *Attorney, Agent, or Firm* — Hamilton, Brook, Smith & Reynolds, P.C.

(57) ABSTRACT

The present invention relates to a palladium-based supported hydrogenation catalyst and a preparation method and application thereof. The catalyst is prepared by the following method: impregnating an $Al_2O_3$-containing carrier with an organic solution containing a bipyridine derivative having hydroxy group, optionally drying followed by impregnating with a mixed solution containing the main active component (Continued)

palladium ions and the auxiliary active component $M^{n+}$ ions, where M is one selected from Ag, Au, Ni, Pb and Cu; and then optionally drying, and calcining to obtain the catalyst. The preparation method provided by the present invention allows Pd atoms and M atoms to be highly uniformly dispersed on the carrier, which overcomes the adverse impact of the surface tension of the impregnation solution and the solvation effect on the dispersibility of active components. The palladium-based supported hydrogenation catalyst provided by the present invention has excellent hydrogenation activity, ethylene selectivity and anti-coking performance, and can be used in a selective hydrogenation process of C2 fraction.

11 Claims, 4 Drawing Sheets

(51) Int. Cl.
*B01J 23/52* (2006.01)
*B01J 23/62* (2006.01)
*B01J 23/89* (2006.01)
*B01J 35/10* (2006.01)
*B01J 35/00* (2006.01)
*B01J 37/02* (2006.01)
*B01J 35/02* (2006.01)
*B01J 37/18* (2006.01)

(52) U.S. Cl.
CPC ......... *B01J 23/892* (2013.01); *B01J 23/8926* (2013.01); *B01J 35/0026* (2013.01); *B01J 35/026* (2013.01); *B01J 35/1009* (2013.01); *B01J 35/1019* (2013.01); *B01J 35/1038* (2013.01); *B01J 35/1042* (2013.01); *B01J 37/0203* (2013.01); *B01J 37/18* (2013.01); *C07C 2521/04* (2013.01); *C07C 2523/44* (2013.01); *C07C 2523/50* (2013.01); *C07C 2523/52* (2013.01); *C07C 2523/62* (2013.01); *C07C 2523/72* (2013.01); *C07C 2523/89* (2013.01); *Y02P 20/52* (2015.11)

(58) Field of Classification Search
CPC ............ C07C 2523/44; C07C 2523/50; C07C 2523/52; C07C 2523/62; C07C 2523/72; C07C 2523/89; C07C 2521/04
See application file for complete search history.

(56) References Cited

U.S. PATENT DOCUMENTS

| | | |
|---|---|---|
| 4,404,124 A | 9/1983 | Johnson et al. |
| 4,714,692 A | 12/1987 | Abrevaya et al. |
| 4,762,956 A | 8/1988 | Liu et al. |
| 5,519,566 A | 5/1996 | Perino et al. |
| 5,587,348 A | 12/1996 | Brown et al. |
| 2009/0030250 A1 | 1/2009 | Hill et al. |
| 2010/0228064 A1* | 9/2010 | Leger .................. B01J 23/38 585/269 |

FOREIGN PATENT DOCUMENTS

| | | |
|---|---|---|
| CN | 104971698 A | 10/2015 |
| CN | 105732261 A | 7/2016 |
| CN | 105732264 A | 7/2016 |
| CN | 105732268 A | 7/2016 |
| CN | 105732271 A | 7/2016 |
| CN | 105777475 A | 7/2016 |
| JP | 2012143742 A | 8/2012 |
| WO | WO-2014176552 A2 * | 10/2014 .............. C07C 45/71 |

OTHER PUBLICATIONS

Sajiki et al., A Novel Type of Pd/C-catalyzed Hydrogenation Using a Catalyst Poison:Chemoselective Inhibition of the Hydrogenolysis for O-Benzyl Protective Group by the Addition of a Nitrogen-containing Base, Tetrahedron 54, 1998, p. 13981-13996.*
Sajiki et al., New aspect of chemoselective hydrogenation utilizing heterogeneous palladium catalysts supported by nitrogen-andoxygen-containing macromolecules, Catalysis Science & Technology, 2014, 4, p. 260-271.*
Onishi et al., CO2 Hydrogenation Catalyzed by Iridium Complexes with a Proton-Responsive Ligand, Inorganic Chemistry, 2015, 54 , p. 5114-5123.*
International Search Report for International Application No. PCT/CN2016/082976, "Palladium-Based Supported Hydrogenation Catalyst and Preparation Method Therefor and Application Thereof", dated Mar. 7, 2017.

* cited by examiner

PALLADIUM-BASED SUPPORTED HYDROGENATION CATALYST, AND PREPARATION METHOD AND APPLICATION THEREOF

RELATED APPLICATIONS

This application is a continuation of International Application No.: PCT/CN2016/082976, which designates the U.S. and was filed on May 23, 2016, published in Chinese. The entire teachings of the above application is incorporated herein by reference.

FIELD OF TECHNOLOGY

The present invention relates to the technical field of hydrogenation catalyst, in particular to a palladium-based supported hydrogenation catalyst and a preparation method and application thereof.

BACKGROUND ART

Ethylene is one of the most important basic material for the petrochemical industry. As a monomer for the synthesis of various polymers, it is generally produced by the steam cracking of petroleum hydrocarbons (e.g., ethane, propane, butane, naphtha, light diesel, and the like). The C2 fraction mainly comprising ethylene obtained in this way also contains 0.5%-2.5% (mole fraction) of acetylene. The presence of acetylene will complicate the polymerization process of ethylene and deteriorate the performances of the polymer. When the polyethylene is produced by a high-pressure process, there may be a risk of explosion due to the accumulation of acetylene. In addition, the presence of acetylene will also decrease the activity of polymerization catalyst and increase the catalyst consumption in the production of polyethylene. Therefore, the acetylene content in ethylene must be reduced below a certain value, so that it can be used as a monomer for the synthesis of polymer. Therefore, the C2 fraction, which is the main product of the ethylene industry, needs to be purified by alkyne hydrogenation before use as a polymerization grade raw material in the production of downstream products such as polyethylene.

Currently, the acetylene in C2 fraction is generally removed by selective hydrogenation and solvent extraction in the industry. The solvent extraction method can not only produce refined vinyl, but also recover the product acetylene. However, the process thereof is complex and difficult to operate. At present, the method of catalytic selective hydrogenation is the most economical and most acceptable method of converting acetylene to ethylene.

During the process of ethylene production, the process of catalytic selective hydrogenation is generally divided into a front-end hydrogenation process and a back-end hydrogenation process. The distinction between the front-end hydrogenation and back-end hydrogenation processes is mainly based on the difference in the location of the hydrogenation reactor. The process where the hydrogenation reactor is located upstream of the demethanizer is called the front-end hydrogenation process. The process where the hydrogenation reactor is located downstream of the demethanizer is called the back-end hydrogenation process. The back-end hydrogenation process is mainly represented by the hydrogenation process developed by ABB Lummus Global, USA, which uses a sequential separation process, i.e., sequentially removing methane and ethane before hydrogenating acetylene in C2 fraction. The back-end hydrogenation process is common in the early introduced domestic ethylene production system. The front-end hydrogenation process is divided into two processes of front-end deethanization hydrogenation and front-end depropanization hydrogenation, which are developed by Linde Group, Germany and Stone & Webster Engineering Corporation, USA, respectively. The hydrogenation reactor for the front-end depropanization hydrogenation process is provided after the depropanizer and before the demethanizer, and the hydrogenation reactor for the front-end deethanization hydrogenation process is provided after the deethanizer and before the demethanizer.

The alkynes and diolefins contained in the C2 and C3 fractions are usually removed by selective hydrogenation. The selective hydrogenation catalyst is obtained by supporting a noble metal, such as palladium, on a porous inorganic material carrier (as described, for example, in U.S. Pat. No. 4,762,956). In U.S. Pat. No. 4,404,124, a selective hydrogenation catalyst having a shell layer of active components is prepared by a step impregnation process and can be applied in the selective hydrogenation of C2 and C3 fractions to eliminate acetylene in ethylene and propyne and propadiene in propylene. In U.S. Pat. No. 5,587,348, an acetylene hydrogenation catalyst having good performances was prepared by combining Ag with Pd on aluminum oxide as a carrier and adding an alkali metal fluoride. The catalyst has the characteristics of reducing the generation of green oil, increasing the selectivity of ethylene and reducing the production of oxygenates. U.S. Pat. No. 5,519,566 discloses a method for preparing silver and palladium catalyst by wet reduction. Silver and palladium bicomponent selective hydrogenation catalyst was prepared by adding organic or inorganic reducing agents into the impregnating solution.

The above conventional selective hydrogenation catalysts are prepared by impregnation methods, and the active components are two metals, Pd and Ag. These methods have the following disadvantages: (1) due to the influence of the pore structure of the carrier, the dispersion of the active components cannot be precisely controlled, with high randomness; (2) due to the influence of surface tension and solvation effect of the impregnating solution, the precursor of the metal active component is deposited on the carrier surface as aggregates and cannot form a uniform distribution. (3) the requirement of C2 fraction hydrogenation on the catalyst selectivity is high, and the interaction between the auxiliary active component Ag and the main active component Pd is the key factor for improving the catalyst selectivity. For the catalyst prepared by the traditional method, due to the different surface tensions of the palladium salt solution and the silver salt solution, the distribution of Pd and Ag in the same layer cannot be formed on the carrier, the auxiliary effect of Ag is not obvious, and it is necessary to increase the amount of Ag to promote the role thereof as an auxiliary, so that the hydrogen transport is hindered and the possibility of the oligomerization reaction is increased, which increases the amount of produced green oil and affects the life of the catalyst. The occurrence of the above three problems tends to result in poor dispersibility of the metal active component and low reaction selectivity, thereby affecting the performance of the catalyst.

U.S. Pat. No. 4,714,692 prepared a single component precious metal catalyst using a microemulsion method. When this method is used to prepare a multicomponent catalyst, the influence of solvation effect on the distribution of active components of the catalyst cannot be avoided.

Both CN102206130A and CN102205243A form a polymer chain coating layer on the surface of a carrier by adsorbing a specific polymer compound on the carrier. A compound having a specific functional group is reacted with the polymer chain on the carrier, so that it has a functional group capable of complexing with the active component. The complexing reaction of the active components on the functional group on the surface of the carrier ensures that the active components are orderly and highly dispersed. When these two methods are used to prepare a catalyst, the carrier adsorbs a specific polymer compound, which is chemically adsorbed by the hydroxy group of the carrier alumina, and the amount of the polymer compounds adsorbed by the carrier will be limited by the number of the hydroxy group of alumina. The complexing of the functionalized polymer chain with palladium ions is not strong. In some cases, the loading of the active components cannot meet the requirement, and some active components remain in the impregnating solution, resulting in the increase of the catalyst cost. Moreover, the use of these two methods to prepare a C2 fraction hydrogenation catalyst also has the drawback of complicated process.

CN104971698A discloses an alumina molded article containing $R_1R_2R_3N^+X^-$ and a preparation method and application thereof, wherein the $R_1R_2R_3N^+X^-$ is selected from one or more of primary amine salts, secondary ammonium salts, tertiary ammonium salts and quaternary ammonium salts, X is selected from chlorine, bromine or iodine, and the substituent may be a linear or branched alkyl group, a cycloalkyl group, an aryl group, or a hydrocarbon group with hydroxy group and/or heterocyclic substituent. The preparation method of the alumina molded article comprises: after molding and drying an alumina-containing carrier, placing it in a high-pressure reactor; heat treating with an appropriate amount of $R_1R_2R_3N^+X^-$ solution at room temperature to 250° C., cooling and drying at 40° C. to 250° C.; and removing excess solvent to produce an alumina carrier containing $R_1R_2R_3N^+X^-$ which has a large specific surface area and a large pore volume. The carrier is particularly suitable for the preparation of a Mo—Ni-based supported hydrogenation catalyst for the hydrogenation of gasoline and diesel, and facilitates the improvement of the hydrodesulfurization activity of the catalyst. However, as for the noble metal Pd-based catalyst, since the organic matter used in this method contains chlorine, bromine or iodine, it tends to form strong acid centers Cl—, Br— and I—on the catalyst surface after activation, resulting in polymerization of unsaturated olefins, alkynes, and diolefins, which lead to the generation of "green oil" in a large amount and a significant increase in catalyst coking and thus affect the service life of the catalyst. Meanwhile, the carrier prepared by this method is one having a large specific surface area and a large pore volume, and is not suitable for the preparation of a Pd-based catalyst with shell distribution.

SUMMARY OF THE INVENTION

In order to solve the above technical problem, an object of the present invention is to provide a palladium-based supported hydrogenation catalyst having more excellent performances and its preparation method and application. The catalyst preparation method provided by the present invention enables the palladium atoms and another kind of metal atoms to be highly uniformly dispersed on the carrier and can overcome the adverse effect on the dispersibility of the active component caused by the surface tension of the impregnation liquid and the solvation effect.

To achieve the above object, firstly, the present invention provides a preparation method of a palladium-based supported hydrogenation catalyst, comprising the steps of: impregnating an $Al_2O_3$-containing carrier with an organic solution containing a bipyridine derivative having hydroxy group, optionally drying followed by impregnating with a mixed solution containing the main active component palladium ions (i.e., 2-valent palladium cations) and the auxiliary active component $M^{n+}$ ions, wherein M is one selected from Ag, Au, Ni, Pb and Cu; and optionally drying, and calcining to obtain the palladium-based supported hydrogenation catalyst.

In the preparation method according to the present invention, the bipyridine derivative having hydroxy group forms a strong adsorption with the $Al_2O_3$-containing carrier and then forms an organic complex with the main active component Pd and the auxiliary active component M metal cations, to finally obtain a Pd-M supported catalyst having highly dispersed active components.

More specifically, the preparation method of a palladium-based supported hydrogenation catalyst according to the present invention comprises the following steps:

(1) impregnating an $Al_2O_3$-containing carrier with an organic solution containing a bipyridine derivative having hydroxy group, and optionally drying (i.e., the drying may be carried out or not carried out), to form a hydroxy-bipyridine/$Al_2O_3$ precursor;

(2) next, impregnating the hydroxy-bipyridine/$Al_2O_3$ precursor with a mixed solution containing the main active component palladium ions and the auxiliary active component $M^{n+}$ ions, and optionally drying (i.e., the drying may be carried out or not carried out), to form a (Pd-M)-hydroxy-bipyridine/$Al_2O_3$ precursor; and (3) calcining the (Pd-M)-hydroxy-bipyridine/$Al_2O_3$ precursor, to obtain the palladium-based supported hydrogenation catalyst.

In the above preparation method, preferably, the impregnation of the $Al_2O_3$-containing carrier with the organic solution containing the bipyridine derivative having hydroxy group (i.e., the above step (1)) is carried out at 20-60° C., and the impregnation duration is 2 to 24 hours. The temperature of the subsequent drying can range from 60° C. to 150° C., and the duration can be 2 to 10 hours.

In the above preparation method, preferably, the impregnation of the hydroxy-bipyridine/$Al_2O_3$ precursor with the mixed solution containing palladium ions and $M^{n+}$ ions (i.e., the above step (2)) is carried out at 20-100° C. (preferably 30-100° C.), and the impregnation duration is 2 to 24 hours. The temperature of the subsequent drying can range from 60° C. to 150° C., and the duration can be 2 to 10 hours.

In the above preparation method, preferably, the temperature of the calcination (i.e., the above step (2)) is from 300° C. to 600° C., and the duration is 2 to 12 hours. More preferably, the calcination temperature is from 350° C. to 600° C. Additionally, the calcination is preferably carried out in an oxygen-containing atmosphere.

In the above preparation method, preferably, the $Al_2O_3$-containing carrier used comprises alumina and/or a mixture containing alumina and an additional oxide, etc. The additional oxide includes a combination of one or more of silica, titania, magnesium oxide and calcium oxide. In addition, the crystal form of $Al_2O_3$ in the carrier can be γ, δ, θ, α, or a mixed crystal form of some of these crystal forms, preferably θ, α or a mixed crystal form thereof.

In the above preparation method, preferably, the $Al_2O_3$-containing carrier used can be in the form of spherical, tooth-spherical, cylindrical, ring, bar, three-leaf clover, four-leaf clover, or the like.

In the above preparation method, preferably, the bipyridine derivative having hydroxy group comprises 2,2'-bipyridine derivative having hydroxy group and/or 3,3'-bipyridine derivative having hydroxy group, more preferably, 2,2'-bipyridine derivative having hydroxy group.

In the preparation method according to the present invention, the solvent in the organic solution containing the bipyridine derivative having hydroxy group may be organic solvents commonly used in the art, such as ethanol and/or diethyl ether. The role of the solvent is to allow the bipyridine derivative having hydroxy group to be completely dissolved, and facilitate its adsorption on the carrier. The amount of the solvent used is not particularly limited, as long as the bipyridine derivative having hydroxy group can be completely dissolved.

In the above preparation method, preferably, the molar ratio of palladium to M in the bipyridine derivative having hydroxy group and the mixed solution containing palladium ions and $M^{n+}$ ions is 1-100:1; more preferably, the molar ratio is 5-80:1; and most preferably, the molar ratio is 20-60:1.

In the above preparation method, preferably, the mixed solution containing palladium ions and $M^{n+}$ ions may be a mixed solution of one or more soluble salts of palladium and one or more soluble salts of M. For example, it can be a mixed solution of $Pd(NO_3)_2$ and $M(NO_3)_n$. The amounts of the palladium salt and the M salt in the mixed solution depend on the desired contents of Pd and M in the catalyst. Preferably, when M is Ag, the molar ratio of Ag to Pd in this mixed solution is 0.4-10:1; when M is Au, the molar ratio of Au to Pd in this mixed solution is 0.5-15:1; when M is Ni, the molar ratio of Ni to Pd in this mixed solution is 0.4-20:1; when M is Pb, the molar ratio of Pb to Pd in this mixed solution is 1-10:1; when M is Cu, the molar ratio of Cu to Pd in this mixed solution is 1-10:1.

In the above preparation method, preferably, the pH of the mixed solution containing palladium ions and $M^{n+}$ ions is 1.5-4.0, more preferably 2.0-4.0. The pH of the mixed solution can be adjusted by using common pH modifiers.

In a preferred specific embodiment of the present invention, the preparation method of the palladium-based supported hydrogenation catalyst can comprise the following steps:

Step (1) Preparation of a Hydroxy-Bipyridine/Al$_2$O$_3$ Precursor

An $Al_2O_3$-containing carrier is impregnated with an organic solution containing a bipyridine derivative having hydroxy group and reacted at 20° C.-60° C. for 2-24 hours, and then the reaction product is optionally dried at 60° C.-150° C. for 2-10 hours, to obtain the hydroxy-bipyridine/$Al_2O_3$ precursor; wherein the volume of the organic solution containing the bipyridine derivative having hydroxy group is preferably 80% or more (including 80%) of the volume of the $Al_2O_3$-containing carrier.

Step (2) Preparation of a (Pd-M)-Hydroxy-Bipyridine/Al$_2$O$_3$ Precursor

The hydroxy-bipyridine/$Al_2O_3$ precursor produced in the Step (1) is impregnated with a mixed solution containing palladium ions and $M^{n+}$ ions at a pH of 1.5-4.0 and reacted at 30° C.-100° C. for 2-24 hours, and the reaction product is optionally dried at 60° C.-150° C. for 2-10 hours, to obtain the (Pd-M)-hydroxy-bipyridine/$Al_2O_3$ precursor (wherein the molar ratio of hydroxy-bipyridine to (Pd+M) is 1-100:1, preferably κ-80:1, more preferably 20-60:1); wherein the volume of this mixed solution is preferably 60%-200% of the volume of the hydroxy-bipyridine/$Al_2O_3$ precursor.

Step (3) Preparation of the Palladium-Based Supported Hydrogenation Catalyst The (Pd-M)-hydroxy-bipyridine/$Al_2O_3$ precursor produced in the Step (2) is calcinated at 300° C.-600° C. for 2-12 hours, to obtain the palladium-based supported hydrogenation catalyst.

In a specific embodiment of the present invention, the preparation method of the palladium-based supported hydrogenation catalyst as described above further comprises the following step: subjecting the palladium-based supported hydrogenation catalyst to a reduction treatment with a hydrogen-containing gas to obtain a reduced palladium-based supported hydrogenation catalyst before use.

In the preparation method according to the present invention, firstly, the Al—O bond in the carrier containing $Al_2O_3$ will strongly adsorb hydroxy group in the bipyridine derivative having hydroxy group so that the bipyridine derivative having hydroxy group would be supported on the carrier to obtain a precursor loaded with a functionalized molecular chain. Then, the remaining hydroxy groups (i.e., the remaining hydroxy group after adsorption with the Al—O bonds) and/or nitrogen groups from the hydroxy bipyridine in the precursor are complexed with the palladium ions and the $M^{n+}$ ions, so that the palladium ions and the $M^{n+}$ ions are bound to the molecular chains adsorbed on the carrier. The complexation reaction is an in situ chemical reaction of the complexing group-metal ion, and the metal ions are bound to the molecular chains by chemical reactions rather than physical adsorption. Thus, Pd and M atoms exhibit a uniform and ordered distribution on the molecular chains, and the number of Pd atoms and M atoms bonded to the molecular chains are proportional to the number of the hydroxy group and nitrogen group on the molecular chains. Thereafter, during the calcination, Pd and M atoms are oxidized in situ to form a Pd-M eutectic composite metal oxide, thereby producing a palladium-based bimetallic supported hydrogenation catalyst.

The preparation method provided by the invention mainly has the following advantages. First of all, since Al—O bonds in the carrier containing $Al_2O_3$ strongly adsorb the hydroxy groups in the bipyridine derivative having hydroxy group, the amount of hydroxy bipyridine adsorbed on the carrier can be effectively ensured, thereby avoiding the loss of the hydroxy bipyridine in the solution. Additionally, since the hydroxy group and nitrogen group of hydroxy bipyridine adsorbed on the carrier have a strong complexing ability with the main active component Pd and the auxiliary active component M, it can be ensured that the palladium ions and the $M^{n+}$ ions in the solution are completely reacted so as to avoid the loss of the active components Pd and M in the solution, reduce the production cost, and allow metal atoms to be highly uniformly dispersed on the carrier. Moreover, the preparation method overcomes the adverse impact of the surface tension of the impregnation liquid and the solvation effect on the dispersion of Pd and M on the carrier. The catalyst prepared by the preparation method of the present invention has excellent hydrogenation activity, ethylene selectivity and anti-coking performance.

In another aspect, the present invention further provides a palladium-based supported hydrogenation catalyst prepared by the preparation method of a palladium-based supported hydrogenation catalyst as described above. The catalyst has excellent hydrogenation activity, ethylene selectivity and anti-coking performance.

According to a specific embodiment of the present invention, preferably, based on 100% by mass of the palladium-based supported hydrogenation catalyst, the content of Pd in the catalyst is 0.01%-0.8%; when M is Ag, its content is 0.03%-3%; when M is Au, its content is 0.02-0.25%; when M is Ni, its content is 0.04-3%; when M is Pb, its content is 0.04-3%; when M is Cu, its content is 0.02-1%.

According to a specific embodiment of the present invention, preferably, the palladium-based supported hydrogenation catalyst has a specific surface area of 1-200 m$^2$/g, a pore volume of 0.15-0.8 mL/g and a bulk density of 0.5-1.2 g/cm$^3$.

In addition, the present invention further provides the use of the palladium-based supported hydrogenation catalyst in the selective hydrogenation process of acetylene.

In the above use, preferably, the acetylene selective hydrogenation process is a selective hydrogenation process of trace acetylene.

In the above use, preferably, the selective hydrogenation process of acetylene comprises a front-end depropanization hydrogenation process of C2 fraction, a front-end deethanization hydrogenation process of C2 fraction, a back-end hydrogenation process of C2 fraction, a selective hydrogenation process of acetylene in the preparation of polymer grade ethylene from ethylene refining, and a selective hydrogenation process of acetylene in the process of Methanol-to-olefin.

In conclusion, the preparation method provided by the invention allows Pd atoms and M atoms to be highly uniformly dispersed on the carrier and overcomes the adverse impact of the surface tension of the impregnation liquid and the solvation effect on the dispersion of active components on the carrier. The palladium-based supported hydrogenation catalyst provided by the present invention has excellent hydrogenation activity, ethylene selectivity and anti-coking performance, and can be used to catalyze the selective hydrogenation of trace acetylene.

DESCRIPTION OF SYMBOLS OF MAIN COMPONENTS

Figure 1:
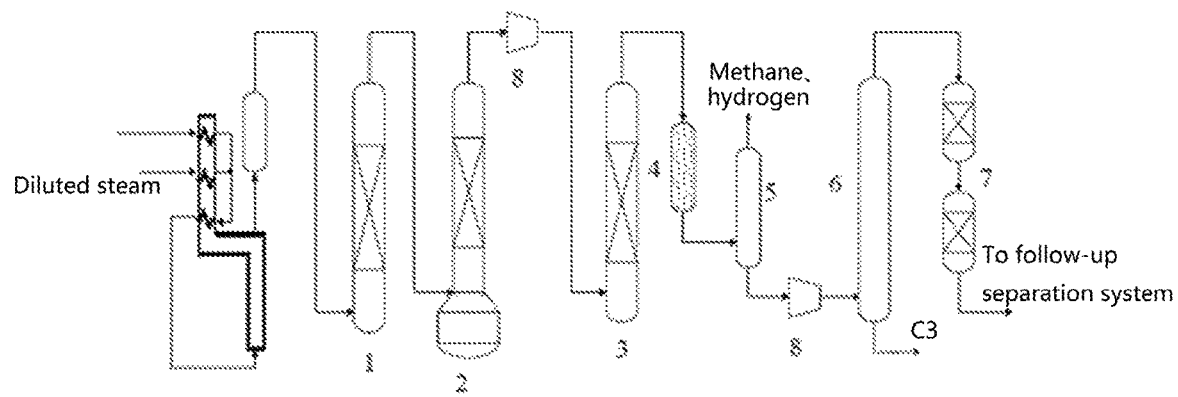
FIG. 1 is a flow chart of a back-end hydrogenation process of C2 fraction with a sequential separation procedure.

1—Oil washing tower, 2—Water washing tower, 3—Alkaline washing tower, 4—Dryer, 5—Demethanizer, 6—Deethanizer, 7—C2 hydrogenation reactor, 8—Compressor, 9—Ethylene refining column, 10—Ethylene refining reactor, 11—Depropanizer, 12—Propylene refining column, 13—Methanol-to-ethylene reactor, 14—Regenerator, 15—Separator, 16—Reactor for dehydration of methanol to dimethyl ether, 17—Methanol-to-propylene reactor, 18—Pre-quench separator, 19—Quench separator, 20—Four-level compressor, 21—Four-level separator.

DETAILED DESCRIPTION OF PREFERRED EMBODIMENTS

Analysis and Testing Methods:
Specific surface area: in accordance with the standard GB/T-5816;
Pore volume: in accordance with the standard GB/T-5816;
Bulk density: in accordance with the standard Q/SY142-2006;
Pd, Ag, Au, Ni, Cu or Pb content in the catalyst: using a plasma emission spectrometer or an atomic absorption spectrometer (in accordance with the standard GB/T 1537-94);
Ethylene selectivity=(the molar percentage of ethylene after reaction—the molar percentage of ethylene prior to reaction)/(the molar percentage of acetylene before reaction—the molar percentage of acetylene after reaction).

EXAMPLE 1

500 g of a spherical α-Al$_2$O$_3$ carrier having Φ3.5 mm, a specific surface area of 20.0 m$^2$/g, a pore volume of 0.48 mL/g and a bulk density of 0.82 g/cm$^3$ was weighed. The pore size of the carrier exhibits a bimodal pore size distribution with pore sizes of 20-50 nm and 300-500 nm, respectively.

34.12 g of 4,4'-dihydroxy-2,2'-bipyridine was dissolved in 650 mL of ethanol to obtain a solution. The above carrier was impregnated in this solution and allowed to stand for 2 hours, to allow 4,4'-dihydroxy-2,2'-bipyridine in the solution to be fully supported on the carrier. Then the solid reaction product was dried at 60° C. for 10 hours, to obtain a hydroxy-bipyridine/Al$_2$O$_3$ precursor.

0.37 g of Pd(NO$_3$)$_2$ and 0.79 g of AgNO$_3$ were dissolved in 600 mL of deionized water and the pH was adjusted to 3.5 with an appropriate amount of nitric acid to obtain a mixed solution. The above hydroxy-bipyridine/Al$_2$O$_3$ precursor was added into the mixed solution, stirred for 10 minutes and allowed to stand for 2 hours. The residual liquid was decanted and the solid reaction product was dried at 120° C. for 4 hours, to obtain a (Pd—Ag)-hydroxy-bipyridine/Al$_2$O$_3$ precursor (wherein the molar ratio of hydroxy-bipyridine to (Pd+Ag) is 30).

The above (Pd—Ag)-hydroxy-bipyridine/Al$_2$O$_3$ precursor was calcined in an air atmosphere at 550° C. for 3 hours to obtain a (Pd—Ag)/Al$_2$O$_3$ catalyst.

The above (Pd—Ag)/Al$_2$O$_3$ catalyst was placed in a fixed-bed reactor, and subjected to a reduction treatment with a hydrogen gas having a purity of 99.9% at a space velocity of 200 h$^{-1}$ at 120° C. for 3 hours, to obtain a reduced palladium-based supported hydrogenation catalyst S–1. The Pd content and the Ag content in this catalyst S–1 were measured to be 0.03 wt. % and 0.10 wt. %, respectively.

COMPARATIVE EXAMPLE 1

500 g of a spherical α-Al$_2$O$_3$ carrier having Φ3.5 mm, a specific surface area of 20.0 m$^2$/g, a pore volume of 0.48 mL/g and a bulk density of 0.82 g/cm³ was weighed. The pore size of the carrier exhibits a bimodal pore size distribution with pore sizes of 20-50 nm and 300-500 nm, respectively.

8.9 g of polyvinyl chloride (PVC) was dissolved in 800 mL of tetrahydrofuran (THF) to obtain a solution. The carrier was impregnated in the solution and allowed to stand for 2 hours, to allow the PVC in the solution to adsorb onto the carrier surface. The solid reaction product was dried at 60° C. for 10 hours, to obtain a PVC/Al$_2$O$_3$ precursor.

19.28 g of dicyandiamide and 4.0 g of Na$_2$CO$_3$ were heated and dissolved in 1000 mL of deionized water, and then the above PVC/Al$_2$O$_3$ precursor was added and reacted under reflux for 1 hour. After cooling to room temperature, the solid reaction product was washed to neutrality with deionized water and then dried at 60° C. for 10 hours, to obtain a functionalized PVC/Al$_2$O$_3$ precursor.

0.37 g of Pd(NO$_3$)$_2$ and 0.79 g of AgNO$_3$ were dissolved in 600 mL of deionized water and the pH was adjusted to 3.5 with an appropriate amount of nitric acid to obtain a mixed solution. The above functionalized PVC/Al$_2$O$_3$ precursor was added into the mixed solution and stirred for 0.5 hours. The residual liquid was decanted. The solid reaction product was washed to neutrality with deionized water and then dried at 120° C. for 4 hours, to obtain a (Pd—Ag)-PVC/Al$_2$O$_3$ precursor.

The above (Pd—Ag)-PVC/Al$_2$O$_3$ precursor was calcinated in an air atmosphere at 550° C. for 2 hours to obtain a (Pd—Ag)/Al$_2$O$_3$ catalyst.

The above (Pd—Ag)/Al$_2$O$_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst D-1. The Pd content and the Ag content in this catalyst D-1 were measured to be 0.03 wt. % and 0.10 wt. %, respectively.

Catalyst Application

The catalysts prepared in Example 1 and Comparative Example 1 were respectively used in the back-end hydrogenation process of C2 fraction with a sequential separation procedure. The process flow chart is shown in FIG. 1. The C2 fraction obtained by steam cracking of petroleum hydrocarbon is treated by sequentially passing through an oil washing tower 1, a water washing tower 2, an alkaline washing tower 3, a dryer 4, a demethanizer 5 and a deethanizer 6 and then entered a C2 hydrogenation reactor 7 for selective hydrogenation to remove traces of acetylene, wherein compressors 8 are provided between the water washing tower 2 and the alkaline washing tower 3 and between the demethanizer 5 and the deethanizer 6.

The reaction was carried out with two C2 hydrogenation reactors in series, i.e., the outlet material of the first section reactor entered the second section reactor. Each reactor has an independent gas dispensing system, and both reactors are fixed-bed adiabatic reactors.

The composition of the C2 materials treated in the C2 hydrogenation reactor was: 1.58% of C$_2$H$_2$, 81.55% of C$_2$H$_4$ and 16.87% of C$_2$H$_6$ (in percentage by volume).

Reaction conditions: the space velocity of the material gas was 2000 h$^{-1}$, the reaction pressure was 1.7 MPa, the catalyst loading in both reactors was 450 mL, H$_2$/C$_2$H$_2$ in the first section reactor=1.5:1 (molar ratio), and H$_2$/C$_2$H$_2$ in the second section reactor=3:1 (molar ratio). The results of the reaction for 500 hours are shown in Table 1.

TABLE 1

| Catalyst | Reactor section | Inlet temperature (° C.) | Temperature rise (° C.) | C$_2$H$_2$ residual amount (v/v %) | Ethylene selectivity (%) | Green oil amount (g) |
|---|---|---|---|---|---|---|
| S-1 | First section | 40 | 28 | 0.15 | 78 | 5.5 |
|  | Second section | 50 | 12 | 0 | 46 | 3.9 |
| D-1 | First section | 40 | 30 | 0.28 | 70 | 9.2 |
|  | Second section | 50 | 16 | 0.11 | 39 | 6.3 |

EXAMPLE 2

500 g of a spherical carrier containing 440 g of θ-Al$_2$O$_3$ and 60 g of titania, having Φ2.5 mm, a specific surface area of 50 m$^2$/g and a pore volume of 0.75 mL/g was weighed.

6.82 g of 4,4'-dihydroxy-2,2'-bipyridine was dissolved in 600 mL of ethanol to obtain a solution. The above carrier was impregnated in this solution and allowed to stand for 8 hours, to allow 4,4'-dihydroxy-2,2'-bipyridine in the solution to be fully supported on the carrier. Then the solid reaction product was dried at 110° C. for 6 hours, to obtain a hydroxy-bipyridine/Al$_2$O$_3$ precursor.

0.38 g of palladium chloride and 1.72 g of chloroauric acid were dissolved in 600 mL of deionized water and the pH was adjusted to 2.5 with an appropriate amount of hydrochloric acid to obtain a mixed solution. The above hydroxy-bipyridine/Al$_2$O$_3$ precursor was added into the mixed solution, stirred for 1 hour and allowed to stand for 8 hours. The residual liquid was decanted, to obtain a (Pd—Au)-hydroxy-bipyridine/Al$_2$O$_3$ precursor (wherein the molar ratio of hydroxy-bipyridine to (Pd+Au) is 5.03).

The above (Pd—Au)-hydroxy-bipyridine/Al$_2$O$_3$ precursor was calcined in an air atmosphere at 500° C. for 6 hours to obtain a (Pd—Au)/Al$_2$O$_3$ catalyst S-2. The Pd content and the Au content in this catalyst were measured to be 0.045 wt. % and 0.20 wt. %, respectively.

COMPARATIVE EXAMPLE 2

500 g of a spherical carrier containing 440 g of θ-Al$_2$O$_3$ and 60 g of titania, having Φ2.5 mm, a specific surface area of 50 m$^2$/g and a pore volume of 0.75 mL/g was weighed.

2.2 g of polystyrene-acrylonitrile (SAN) was added to 600 mL dimethylformamide (DMF), and stirred at room temperature until the SAN was completely dissolved to obtain a solution. The above carrier was added to the solution, fully stirred and allowed to stand for 1 hour. The solid reaction product was dried at 120° C. for 6 hours, to obtain a SAN/Al$_2$O$_3$ precursor.

The above SAN/Al$_2$O$_3$ precursor was added into 1000 mL of deionized water, and 57.6 g of ethylenediamine was added, stirred until the precursor was completely dissolved and then reacted under reflux for 1 hour. After cooling to room temperature, the solid reaction product was washed to neutrality with deionized water and then dried at 80° C. for 5 hours, to obtain a functionalized SAN/Al$_2$O$_3$ precursor.

0.38 g of palladium chloride and 1.72 g of chloroauric acid were dissolved in 1200 mL of deionized water and the pH was adjusted to 2.5 with an appropriate amount of hydrochloric acid to obtain a mixed solution. The above functionalized SAN/Al$_2$O$_3$ precursor was added into the mixed solution and stirred for 2 hours. The residual liquid was decanted and the solid reaction product was washed to neutrality with deionized water, to obtain a (Pd—Au)-SAN/Al$_2$O$_3$ precursor.

The above (Pd—Au)-SAN/Al$_2$O$_3$ precursor was calcined in an air atmosphere at 380° C. for 2 hours to obtain a (Pd—Au)/Al$_2$O$_3$ catalyst D-2. The Pd content and the Au content in this catalyst were measured to be 0.045 wt. % and 0.20 wt. %, respectively.

Catalyst Application

The catalysts prepared in Example 2 and Comparative Example 2 were respectively used in the back-end hydrogenation process of C2 fraction with a sequential separation procedure. The process flow chart is shown in FIG. 1.

The reaction was carried out with two C2 hydrogenation reactors in series, i.e., the outlet material of the first section reactor entered the second section reactor. Each reactor has an independent gas dispensing system, and both reactors are fixed-bed adiabatic reactors.

The composition of the C2 materials treated in the C2 hydrogenation reactor was: 1.7% of C$_2$H$_2$, 74.3% of C$_2$H$_4$ and 24.0% of C$_2$H$_6$ (in percentage by volume).

Reaction conditions: the space velocity of the material gas was 4000 h$^{-1}$, the reaction pressure was 1.2 MPa, the catalyst loading for both reactors was 500 mL, H$_2$/C$_2$H$_2$ in the first section reactor=1.6:1 (molar ratio), and H$_2$/C$_2$H$_2$ in the second section reactor=2.8:1 (molar ratio). The results of the reaction for 1000 hours are shown in Table 2.

TABLE 2

| Catalyst | Reactor section | Inlet temperature (° C.) | Temperature rise (° C.) | C$_2$H$_2$ residual amount (v/v %) | Ethylene increment (mol %) | Ethylene selectivity (%) | Green oil amount (g) |
|---|---|---|---|---|---|---|---|
| S-2 | First section | 38 | 16 | 0.14 | 1.2 | 85 | 7.0 |
|  | Second section | 45 | 5 | 0 |  | 50 | 3.0 |
| D-2 | First section | 40 | 20 | 0.34 | 0.5 | 65 | 10.6 |
|  | Second section | 50 | 10 | 0.09 |  | 32 | 6.7 |

EXAMPLE 3

500 g of a cylindrical carrier containing 400 g of α-Al$_2$O$_3$ and 100 g of magnesium oxide, having Φ4.5 mm, a height of 4.5 mm, a specific surface area of 17 m$^2$/g and a pore volume of 0.33 mL/g was weighed.

82.65 g of 6,6'-dihydroxy-3,3'-bipyridine was dissolved in 650 mL of ethanol to obtain a solution. The above carrier was impregnated in this solution and allowed to stand for 12 hours, to allow 6,6'-dihydroxy-3,3'-bipyridine in the solution to be fully supported on the carrier, the solid reaction product was dried at 120° C. for 4 hours, to obtain a hydroxy-bipyridine/Al$_2$O$_3$ precursor.

0.68 g of Pd(NO$_3$)$_2$ and 2.43 g of Ni(NO$_3$)$_2$.6H$_2$O were dissolved in 600 mL of deionized water and the pH was adjusted to 3.4 with an appropriate amount of nitric acid to obtain a mixed solution. The above hydroxy-bipyridine/Al$_2$O$_3$ precursor was added into the mixed solution, stirred for 60 minutes and allowed to stand for 10 hours. The residual liquid was decanted, to obtain a (Pd—Ni)-hydroxy-bipyridine/Al$_2$O$_3$ precursor (wherein the molar ratio of hydroxy-bipyridine to (Pd+Ni) is 40).

The above (Pd—Ni)-hydroxy-bipyridine/Al$_2$O$_3$ precursor was calcined in an air atmosphere at 450° C. for 8 hours to obtain a (Pd—Ni)/Al$_2$O$_3$ catalyst.

The above (Pd—Ag)/Al$_2$O$_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst S-3. The Pd content and the Ni content in this catalyst S-3 were measured to be 0.056 wt. % and 0.098 wt. %, respectively.

COMPARATIVE EXAMPLE 3

500 g of a cylindrical carrier containing 400 g of α-Al$_2$O$_3$ and 100 g of magnesium oxide, having Φ4.5 mm, a height of 4.5 mm, a specific surface area of 17 m$^2$/g and a pore volume of 0.33 mL/g was weighed.

8.9 g of polyvinyl chloride (PVC) was dissolved in 800 mL of tetrahydrofuran (THF) to obtain a solution. The above carrier was impregnated in the solution and allowed to stand for 2 hours, to allow the PVC in the solution to adsorb onto the carrier surface. The solid reaction product was dried at 60° C. for 10 hours, to obtain a PVC/Al$_2$O$_3$ precursor.

19.28 g of dicyandiamide and 4.0 g of Na$_2$CO$_3$ were heated and dissolved in 1000 mL of deionized water, and then the above PVC/Al$_2$O$_3$ precursor was added and reacted under reflux for 1 hour. After cooling to room temperature, the solid reaction product was washed to neutrality with deionized water and then dried at 60° C. for 10 hours, to obtain a functionalized PVC/Al$_2$O$_3$ precursor.

0.68 g of Pd(NO$_3$)$_2$ and 2.43 g of Ni(NO$_3$)$_2$.6H$_2$O were dissolved in 2400 mL of deionized water and the pH was adjusted to 3.4 with an appropriate amount of nitric acid to obtain a mixed solution. The above functionalized PVC/Al$_2$O$_3$ precursor was added into the mixed solution and stirred for 0.5 hours. The residual liquid was decanted. The solid reaction product was washed to neutrality with deionized water and then dried at 120° C. for 4 hours, to obtain a (Pd—Ni)-PVC/Al$_2$O$_3$ precursor.

The above (Pd—Ni)-PVC/Al$_2$O$_3$ precursor was calcined in an air atmosphere at 450° C. for 8 hours to obtain a (Pd—Ni)/Al$_2$O$_3$ catalyst.

The above (Pd—Ni)/Al$_2$O$_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst D-3. The Pd content and the Ni content in this catalyst D-3 were measured to be 0.056 wt. % and 0.098 wt. %, respectively.

Catalyst Application

Figure 2:
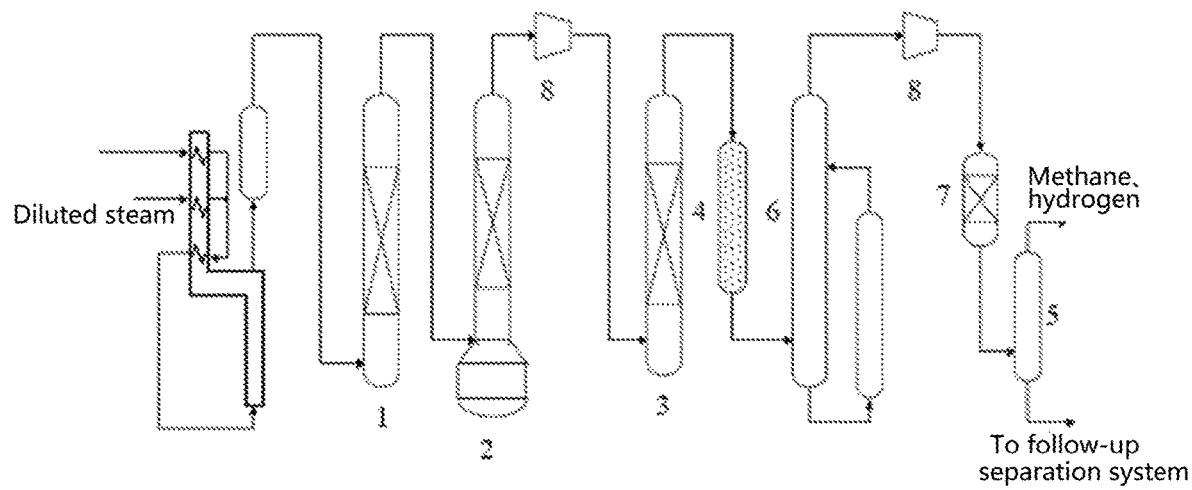
FIG. 2 is a flow chart of a front-end deethanization hydrogenation process of C2 fraction.

The catalysts prepared in Example 3 and Comparative Example 3 were respectively used in the front-end deethanization process of C2 fraction. The process flow chart is shown in FIG. 2. The C2 fraction obtained by steam cracking of petroleum hydrocarbon is treated by sequentially passing through an oil washing tower 1, a water washing tower 2, an alkaline washing tower 3, a dryer 4 and a deethanizer 6 and then entered a C2 hydrogenation reactor 7 for selective hydrogenation to remove traces of acetylene, followed by treatment in a demethanizer 5, wherein compressors 8 are provided between the water washing tower 2 and the alkaline washing tower 3 and between the deethanizer 6 and the C2 hydrogenation reactor 7.

The reaction was carried out with one C2 hydrogenation reactor. The reactor has a gas dispensing system and is a fixed-bed adiabatic reactor.

The reaction materials come from the top of the deethanizer and the composition thereof is shown in Table 3.

TABLE 3

| | Raw materials for hydrogenation | | | | | |
|---|---|---|---|---|---|---|
| | $H_2$ | $C_2H_2$ | $C_2H_4$ | $C_2H_6$ | $CH_4$ | CO |
| Content (v/v %) | 25.32 | 0.5 | 34.3 | 8.88 | 31 | 0.005 |

Reaction conditions: the space velocity of the material gas is 7000 $h^{-1}$, the reaction pressure is 3.0 MPa, and the catalyst loading for the reactors is 500 mL. The results of the reaction for 500 hours are shown in Table 4.

TABLE 4

| Catalyst | Inlet temperature (° C.) | Temperature rise (° C.) | $C_2H_2$ residual amount (v/v %) | Ethylene selectivity (%) | Green oil amount (wt. %) |
|---|---|---|---|---|---|
| S-3 | 100 | 41 | 0.02 | 54 | 0.5 |
| D-3 | 100 | 44 | 0.08 | 32 | 2.0 |

EXAMPLE 4

500 g of a spherical α-$Al_2O_3$ carrier having Φ2.4 mm, a specific surface area of 18.0 $m^2$/g and a pore volume of 0.16 mL/g was weighed.

53.26 g of 4,4'-dihydroxy-2,2'-bipyridine was dissolved in 600 mL of ethanol to obtain a solution. The above carrier was impregnated in this solution and allowed to stand for 16 hours, to allow 4,4'-dihydroxy-2,2'-bipyridine to be fully supported on the carrier. Then the solid reaction product was dried at 120° C. for 5 hours, to obtain a hydroxy-bipyridine/$Al_2O_3$ precursor.

0.61 g of Pd($NO_3$)$_2$ and 3.90 g of Pb($NO_3$)$_2$ were dissolved in 600 mL of deionized water and the pH was adjusted to 3.5 with an appropriate amount of nitric acid to obtain a mixed solution. The above hydroxy-bipyridine/$Al_2O_3$ precursor was added into the mixed solution, stirred for 10 minutes and allowed to stand for 12 hours. The residual liquid was decanted and the solid reaction product was dried at 90° C. for 8 hours, to obtain a (Pd—Pb)-hydroxy-bipyridine/$Al_2O_3$ precursor (wherein the molar ratio of hydroxy-bipyridine to (Pd+Pb) is 20).

The above (Pd—Pb)-hydroxy-bipyridine/$Al_2O_3$ precursor was calcined in an air atmosphere at 450° C. for 8 hours to obtain a (Pd—Pb)/$Al_2O_3$ catalyst.

The above (Pd—Pb)/$Al_2O_3$ catalyst was placed in a fixed-bed reactor, and subjected to a reduction treatment at 115° C. for 3 hours with a mixed gas of $N_2$:$H_2$ in a molar ratio of 1:1 at a space velocity of 200 $h^{-1}$, to obtain a reduced palladium-based supported hydrogenation catalyst S-4. The Pd content and the Pb content in this catalyst S-4 were measured to be 0.05 wt. % and 0.48 wt. %, respectively.

COMPARATIVE EXAMPLE 4

500 g of a spherical α-$Al_2O_3$ carrier having Φ2.4 mm, a specific surface area of 18.0 $m^2$/g and a pore volume of 0.16 mL/g was weighed.

3.3 g of polystyrene-acrylonitrile (SAN) was added to 600 mL dimethylformamide (DMF), and stirred at room temperature until the SAN was completely dissolved to obtain a solution. The above carrier was added to the solution, fully stirred and allowed to stand for 1 hour. The solid reaction product was dried at 120° C. for 6 hours, to obtain a SAN/$Al_2O_3$ precursor.

The above SAN/$Al_2O_3$ precursor was added into 1000 mL of deionized water, and 85.2 g of ethylenediamine was added, stirred until the precursor was completely dissolved and reacted under reflux for 1 hour. After cooling to room temperature, the solid reaction product was washed to neutrality with deionized water and then dried at 80° C. for 5 hours, to obtain a functionalized SAN/$Al_2O_3$ precursor.

0.61 g of Pd($NO_3$)$_2$ and 3.90 g of Pb($NO_3$)$_2$ were dissolved in 1200 mL of deionized water and the pH was adjusted to 2.7 with an appropriate amount of nitric acid to obtain a mixed solution. The above functionalized SAN/$Al_2O_3$ precursor was added into the mixed solution and stirred for 2 hours. The residual liquid was decanted and the solid reaction product was washed to neutrality with deionized water, to obtain a (Pd—Pb)-SAN/$Al_2O_3$ precursor.

The above (Pd—Pb)-SAN/$Al_2O_3$ precursor was calcined in an air atmosphere at 450° C. for 8 hours to obtain a (Pd—Pb)/$Al_2O_3$ catalyst.

The above (Pd—Pb)/$Al_2O_3$ catalyst was placed in a fixed-bed reactor, and subjected to a reduction treatment at 115° C. for 3 hours with a mixed gas of $N_2$:$H_2$ in a molar ratio of 1:1 at a space velocity of 200 $h^{-1}$, to obtain a reduced palladium-based supported hydrogenation catalyst D-4. The Pd content and the Pb content in this catalyst D-4 were measured to be 0.05 wt. % and 0.48 wt. %, respectively.

Catalyst Application

Figure 3:
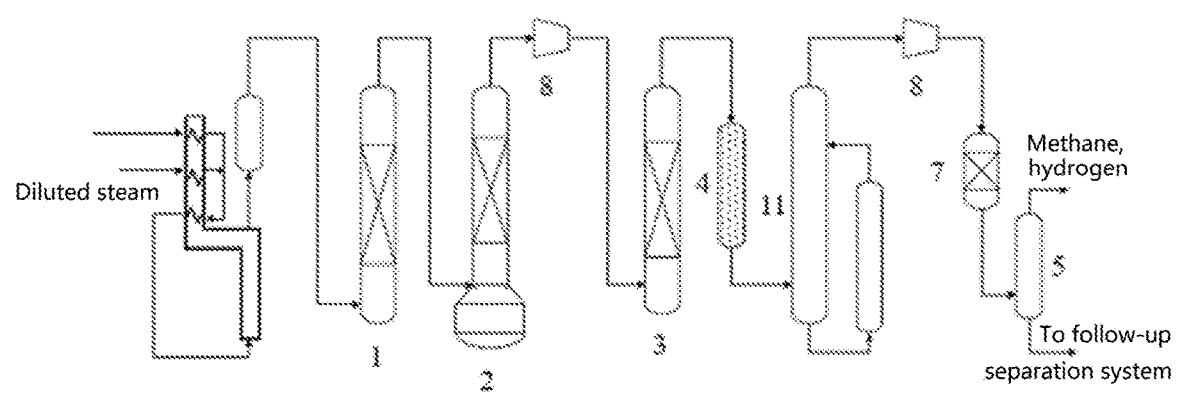
FIG. 3 is a flow chart of a front-end depropanization hydrogenation process of C2 fraction.

The catalysts prepared in Example 4 and Comparative Example 4 were respectively used in the front-end depropanization hydrogenation process of C2 fraction. The process flow chart is shown in FIG. 3. The C2 fraction obtained by steam cracking of petroleum hydrocarbon is treated by sequentially passing through an oil washing tower 1, a water washing tower 2, an alkaline washing tower 3, a dryer 4 and a depropanizer 11 and then entered a C2 hydrogenation reactor 7 for selective hydrogenation to remove traces of acetylene, followed by treatment in a demethanizer 5, wherein compressors 8 were provided between the water washing tower 2 and the alkaline washing tower 3 and between the depropanizer 11 and the C2 hydrogenation reactor 7.

The reaction was carried out with two C2 hydrogenation reactors in series, i.e., the outlet material of the first section reactor entered the second section reactor. Each reactor has an independent gas dispensing system, and both reactors are fixed-bed adiabatic reactors.

The reaction materials come from the top of the depropanizer and the composition thereof is shown in Table 5.

TABLE 5

| Raw materials for hydrogenation | | | | | | | | | |
|---|---|---|---|---|---|---|---|---|---|
| $H_2$ | $C_2H_2$ | $C_2H_4$ | $C_2H_6$ | $CH_4$ | $C_3H_6$ | $C_3H_8$ | PDMA | CO | $C_4+$ |
| Content (v/v %) 18 | 0.6 | 33 | 6.2 | 26.2 | 13 | 2 | 0.8 | 0.2 | 0.47 |

Reaction conditions: the space velocity of the material gas is 4000 h$^{-1}$, the reaction pressure is 3.5 MPa, and the catalyst loading for both reactors is 500 mL. The results of the reaction for 200 hours are shown in Table 6.

TABLE 6

| Catalyst | Period | Reactor section | Inlet temperature (° C.) | Temperature rise (° C.) | $C_2H_2$ residual amount (v/v %) | Ethylene selectivity (%) | Green oil amount (wt. %) |
|---|---|---|---|---|---|---|---|
| S-4 | 0-50 h | First section | 80 | 20 | 0.23 | 82 | 1.9 |
|  |  | Second section | 90 | 11 | 0.01 | 51 | 1.3 |
| D-4 | 0-50 h | First section | 80 | 25 | 0.48 | 35 | 7.0 |
|  |  | Second section | 90 | 16 | 0.20 | 30 | 4.1 |
| S-4 | 50-100 h | First section | 80 | 20 | 0.21 | 82 | 2.6 |
|  |  | Second section | 90 | 11 | 0.01 | 65 | 1.5 |
| D-4 | 50-100 h | First section | 80 | 25 | 0.28 | 66 | 9.0 |
|  |  | Second section | 90 | 18 | 0.09 | 45 | 4.9 |
| S-4 | 100-150 h | First section | 80 | 20 | 0.22 | 86 | 2.6 |
|  |  | Second section | 90 | 11 | 0.02 | 68 | 1.4 |
| D-4 | 100-150 h | First section | 80 | 20 | 0.65 | 63 | 9.9 |
|  |  | Second section | 90 | 16 | 0.20 | 45 | 6.2 |

EXAMPLE 5

500 g of a tooth-spherical α-Al$_2$O$_3$ carrier containing 460 g of θ-Al$_2$O$_3$ and 40 g of titania, having Φ4.2 mm, a specific surface area of 45.0 m$^2$/g, a pore volume of 0.35 mL/g and a bulk density of 0.77 g/cm$^3$ was weighed. The pore size of the carrier exhibits a bimodal pore size distribution with pore sizes of 20-35 nm and 200-450 nm, respectively.

15.79 g of 6,6'-dihydroxy-3,3'-bipyridine was dissolved in 650 mL of ethanol to obtain a solution. The above carrier was impregnated in this solution and allowed to stand for 12 hours, to allow 6,6'-dihydroxy-3,3'-bipyridine in the solution to be fully supported on the carrier, the solid reaction product was dried at 120° C. for 4 hours, to obtain a hydroxy-bipyridine/Al$_2$O$_3$ precursor.

0.25 g of Pd(NO$_3$)$_2$ and 0.59 g of Cu(NO$_3$)$_2$ were dissolved in 600 mL of deionized water and the pH was adjusted to 2.1 with an appropriate amount of nitric acid to obtain a mixed solution. The above hydroxy-bipyridine/Al$_2$O$_3$ precursor was added into the mixed solution, stirred for 1 hour and allowed to stand for 8 hours. The residual liquid was decanted and the solid reaction product was dried at 100° C. for 8 hours, to obtain a (Pd—Cu)-hydroxy-bipyridine/Al$_2$O$_3$ precursor (wherein the molar ratio of hydroxy-bipyridine to (Pd+Cu) is 20).

The above (Pd—Cu)-hydroxy-bipyridine/Al$_2$O$_3$ precursor was calcined in an air atmosphere at 450° C. for 6 hours to obtain a (Pd+Cu)/Al$_2$O$_3$ catalyst.

The above (Pd—Cu)/Al$_2$O$_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst S–5. The Pd content and the Cu content in this catalyst S–5 were measured to be 0.02 wt. % and 0.04 wt. %, respectively.

COMPARATIVE EXAMPLE 5

500 g of a tooth-spherical α-Al$_2$O$_3$ carrier containing 460 g of θ-Al$_2$O$_3$ and 40 g of titania, having Φ4.2 mm, a specific surface area of 45.0 m$^2$/g, a pore volume of 0.35 mL/g and a bulk density of 0.77 g/cm$^3$ was weighed. The pore size of the carrier exhibits a bimodal pore size distribution with pore sizes of 20-35 nm and 200-450 nm, respectively.

16.0 g of chlorinated polyethylene (CPE) was dissolved in 800 mL of tetrahydrofuran (THF), and 480 g of dicyandiamide and 4.0 g of Na$_2$CO$_3$ were added, stirred until they were completely dissolved and reacted under reflux for 2 hours. After cooling to room temperature, the solid reaction product was washed to neutrality with deionized water, to obtain a functionalized CPE solution.

0.25 g of Pd(NO$_3$)$_2$, 0.59 g of Cu(NO$_3$)$_2$ and 1 mL of nitric acid were added to the functionalized CPE solution and stirred for 1 hour, to obtain a (Pd—Cu)-CPE precursor solution.

The above carrier was added to the (Pd—Cu)-CPE precursor solution, fully stirred and allowed to stand for 4 hours. The residual liquid was decanted. The solid reaction product was washed to neutrality with deionized water and then dried at 100° C. for 8 hours, to obtain a (Pd—Cu)-CPE/Al$_2$O$_3$ precursor.

The above (Pd—Cu)-CPE/Al$_2$O$_3$ precursor was calcined in an air atmosphere at 450° C. for 8 hours to obtain a (Pd—Cu)/Al$_2$O$_3$ catalyst.

The above (Pd—Cu)/Al$_2$O$_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst D–5. The Pd content and the Cu content in this catalyst D–5 were measured to be 0.02 wt. % and 0.04 wt. %, respectively.

Catalyst Application

The catalysts prepared in Example 5 and Comparative Example 5 were respectively used in the front-end depropanization hydrogenation process of C2 fraction. The process flow chart is shown in FIG. 3.

The reaction was carried out with two C2 hydrogenation reactors in series, i.e., the outlet material of the first section reactor entered the second section reactor. Each reactor has an independent gas dispensing system, and both reactors are fixed-bed adiabatic reactors.

The reaction materials come from the top of the depropanizer and the composition thereof is shown in Table 7.

TABLE 7

| | Raw materials for hydrogenation | | | | | | | | |
|---|---|---|---|---|---|---|---|---|---|
| | H$_2$ | C$_2$H$_2$ | C$_2$H$_4$ | C$_2$H$_6$ | CH$_4$ | C$_3$H$_6$ | C$_3$H$_8$ | PDMA | CO | C$_4$+ |
| Content (v/v %) | 18.0 | 0.7 | 35.6 | 6.2 | 24.5 | 11 | 3.0 | 0.6 | 0.2 | 0.3 |

Reaction conditions: the space velocity of the material gas is 8000 h$^{-1}$, the reaction pressure is 3.6 MPa, the catalyst loading for both reactors is 500 mL, and the results of the reaction for 1000 hours are shown in Table 8.

TABLE 8

| Catalyst | Reactor section | Inlet temperature (° C.) | Temperature rise (° C.) | C$_2$H$_2$ residual amount (v/v %) | Ethylene selectivity (%) | Green oil amount (wt. %) |
|---|---|---|---|---|---|---|
| S–5 | First section | 75 | 23 | 0.28 | 75 | 4.3 |
| | Second section | 80 | 14 | 0.02 | 46 | 1.1 |
| D–5 | First section | 75 | 27 | 0.45 | 37 | 8.8 |
| | Second section | 80 | 18 | 0.16 | 22 | 3.8 |

EXAMPLE 6

500 g of a spherical α-Al$_2$O$_3$ carrier having Φ4.0 mm, a specific surface area of 20.0 m$^2$/g, a pore volume of 0.48 mL/g and a bulk density of 0.87 g/cm$^3$ was weighed. The pore size of the carrier exhibits a bimodal pore size distribution with pore sizes of 20-50 nm and 200-500 nm, respectively.

167.81 g of 4,4'-dihydroxy-2,2'-bipyridine was dissolved in 650 mL of ethanol to obtain a solution. The above carrier was impregnated in this solution and allowed to stand for 2 hours, to allow 4,4'-dihydroxy-2,2'-bipyridine in the solution to be fully supported on the Al$_2$O$_3$ carrier. Then the solid reaction product was dried at 60° C. for 10 hours, to obtain a hydroxy-bipyridine/Al$_2$O$_3$ precursor.

0.49 g of Pd(NO$_3$)$_2$ and 1.57 g of AgNO$_3$ were dissolved in 600 mL of deionized water and the pH was adjusted to 2.7 with an appropriate amount of nitric acid to obtain a mixed solution. The above hydroxy-bipyridine/Al$_2$O$_3$ precursor was added into the mixed solution, stirred for 10 minutes and allowed to stand for 2 hours. The residual liquid was decanted and the solid reaction product was dried at 120° C. for 4 hours, to obtain a (Pd—Ag)-hydroxy-bipyridine/Al$_2$O$_3$ precursor (wherein the molar ratio of hydroxy-bipyridine to (Pd+Ag) is 80).

The above (Pd—Ag)-hydroxy-bipyridine/Al$_2$O$_3$ precursor was calcined in an air atmosphere at 550° C. for 2 hours to obtain a (Pd—Ag)/Al$_2$O$_3$ catalyst.

The above (Pd—Ag)/Al$_2$O$_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst S–6. The Pd content and the Ag content in this catalyst S–6 were measured to be 0.04 wt. % and 0.20 wt. %, respectively.

COMPARATIVE EXAMPLE 6

500 g of a spherical α-Al$_2$O$_3$ carrier having Φ4.0 mm, a specific surface area of 20.0 m$^2$/g, a pore volume of 0.48 mL/g and a bulk density of 0.87 g/cm$^3$ was weighed. The pore size of the carrier exhibits a bimodal pore size distribution with pore sizes of 20-50 nm and 200-500 nm, respectively.

8.9 g of polyvinyl chloride (PVC) was dissolved in 800 mL of tetrahydrofuran (THF) to obtain a solution. The above carrier was impregnated in the solution and allowed to stand for 2 hours, to allow the PVC in the solution to adsorb onto the carrier surface. The solid reaction product was dried at 90° C. for 6 hours, to obtain a PVC/Al$_2$O$_3$ precursor.

119.28 g of dicyandiamide and 4.0 g of Na$_2$CO$_3$ were heated and dissolved in 1000 mL of deionized water, and then the above PVC/Al$_2$O$_3$ precursor was added and reacted under reflux for 1 hour. After cooling to room temperature, the solid reaction product was washed to neutrality with deionized water and then dried at 60° C. for 10 hours, to obtain a functionalized PVC/Al$_2$O$_3$ precursor.

0.49 g of Pd(NO$_3$)$_2$ and 1.57 g of AgNO$_3$ were dissolved in 200 mL of deionized water and the pH was adjusted to 2.7 with an appropriate amount of nitric acid to obtain a mixed solution. The above functionalized PVC/Al$_2$O$_3$ precursor was added into the mixed solution and stirred for 0.5 hours. The residual liquid was decanted. The solid reaction product was washed to neutrality with deionized water and then dried at 120° C. for 4 hours, to obtain a (Pd—Ag)-PVC/Al$_2$O$_3$ precursor.

The above (Pd—Ag)-PVC/Al$_2$O$_3$ precursor was calcined in an air atmosphere at 550° C. for 2 hours to obtain a (Pd—Ag)/Al$_2$O$_3$ catalyst.

The above (Pd—Ag)/Al$_2$O$_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst D-6. The Pd content and the Ag content in this catalyst D-6 were measured to be 0.038 wt. % and 0.19 wt. %, respectively.

Catalyst Application

Figure 4:
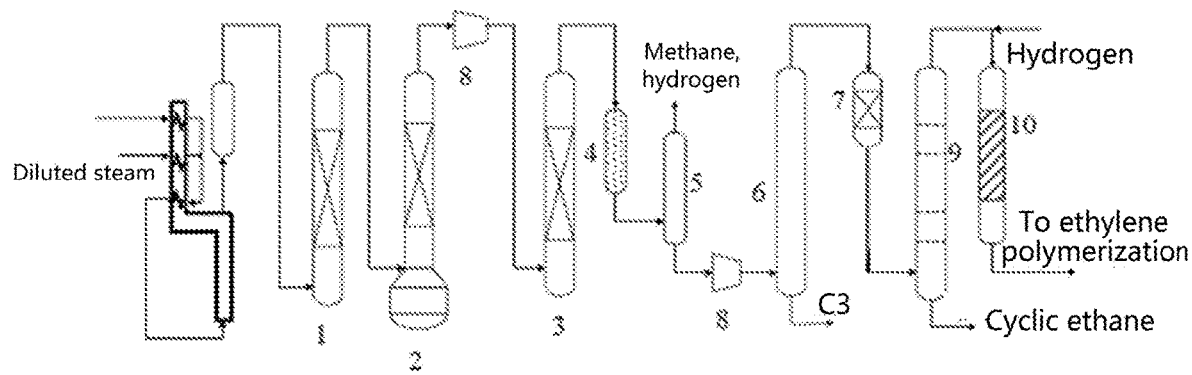
FIG. 4 is a flow chart of an ethylene refining process with a sequential separation procedure.

The catalysts prepared in Example 6 and Comparative Example 6 were respectively used in the ethylene refining process with a sequential separation procedure. The process flow chart is shown in FIG. 4. The C2 fraction obtained by steam cracking of petroleum hydrocarbon is treated by sequentially passing through an oil washing tower 1, a water washing tower 2, an alkaline washing tower 3, a dryer 4, a demethanizer 5 and a deethanizer 6 and then entered a C2 hydrogenation reactor 7 for selective hydrogenation to remove traces of acetylene, and then treated by sequentially passing through an ethylene refining column 9 and an ethylene refining reactor 10, wherein compressors 8 were provided between the water washing tower 2 and the alkaline washing tower 3 and between the demethanizer 5 and the deethanizer 6.

The reaction was carried out with one C2 hydrogenation reactor. The reactor has a gas dispensing system and is a fixed-bed adiabatic reactor.

The content of C$_2$H$_2$ in the reaction material entering the C2 hydrogenation reactor was 5 µL/L.

Reaction conditions: the space velocity of the material gas is 2500 h$^{-1}$, the reaction pressure is 2.0 MPa, the catalyst loading for the reactor is 200 mL, and the content of H$_2$ in the reactor is 10 µL/L. The results of the reaction for 500 hours are shown in Table 9.

TABLE 9

| catalyst | Reactor inlet temperature (° C.) | Temperature rise (° C.) | C$_2$H$_2$ residual amount (µL/L) | Ethylene selectivity (%) | Green oil amount (g) |
|---|---|---|---|---|---|
| S-6 | 35 | 4 | 0 | 55 | 0.8 |
| D-6 | 35 | 6 | 1.4 | 37 | 1.9 |

EXAMPLE 7

500 g of a cylindrical δ-Al$_2$O$_3$ carrier having Φ3.5 mm, a height of 3.5 mm, a specific surface area of 47.0 m$^2$/g, a pore volume of 0.30 mL/g and a bulk density of 0.70 g/cm$^3$ was weighed. The carrier after modification with alkaline earth element Mg has a Mg content of 0.35 wt. %. The pore size of the carrier exhibits a bimodal pore size distribution with pore sizes of 20-30 nm and 100-450 nm, respectively.

5.30 g of 4,4'-dihydroxy-2,2'-bipyridine was dissolved in 600 mL of ethanol to obtain a solution. The above carrier was impregnated in this solution and allowed to stand for 10 hours, to allow 4,4'-dihydroxy-2,2'-bipyridine in the solution to be fully supported on the carrier. Then the solid reaction product was dried at 100° C. for 6 hours, to obtain a hydroxy-bipyridine/Al$_2$O$_3$ precursor.

0.61 g of Pd(NO$_3$)$_2$ and 0.21 g of chloroauric acid were dissolved in 600 mL of deionized water and the pH was adjusted to 3.0 with an appropriate amount of nitric acid to obtain a mixed solution. The above hydroxy-bipyridine/Al$_2$O$_3$ precursor was added into the mixed solution, stirred for 1 hour and allowed to stand for 10 hours. The residual liquid was decanted and the solid reaction product was dried at 90° C. for 10 hours, to obtain a (Pd—Au)-hydroxy-bipyridine/Al$_2$O$_3$ precursor (wherein the molar ratio of hydroxy-bipyridine to (Pd+Au) is 10).

The above (Pd—Au)-hydroxy-bipyridine/Al$_2$O$_3$ precursor was calcined in an air atmosphere at 600° C. for 2 hours to obtain a (Pd—Au)/Al$_2$O$_3$ catalyst.

The above (Pd—Au)/Al$_2$O$_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst S-7. The Pd content and the Au content in this catalyst S-7 were measured to be 0.05 wt. % and 0.02 wt. %, respectively.

COMPARATIVE EXAMPLE 7

500 g of a cylindrical δ-Al$_2$O$_3$ carrier having Φ3.5 mm, a height of 3.5 mm, a specific surface area of 47.0 m$^2$/g, a pore volume of 0.30 mL/g and a bulk density of 0.70 g/cm$^3$ was weighed. The carrier after modification with alkaline earth element Mg has a Mg content of 0.35 wt. %. The pore size of the carrier exhibits a bimodal pore size distribution with pore sizes of 20-30 nm and 100-450 nm, respectively.

0.61 g of Pd(NO$_3$)$_2$ was added to 300 mL of deionized water, and the pH was adjusted to 2.5 with an appropriate amount of nitric acid to obtain a solution. The above carrier was added to the solution and stirred for 5 minutes. The residual liquid was decanted and the solid reaction product was dried at 110° C. for 6 hours, to obtain a Pd/Al$_2$O$_3$ precursor.

0.21 g of chloroauric acid was dissolved in 600 mL of deionized water to obtain a solution. The above Pd/Al$_2$O$_3$ precursor was added to the solution and stirred for 5 minutes. The residual liquid was decanted. The solid reaction product was dried at 110° C. for 6 hours and then calcined in an air atmosphere at 500° C. for 4 hours to obtain a (Pd—Pb)/Al$_2$O$_3$ catalyst.

The above (Pd—Au)/Al$_2$O$_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst D-7. The Pd content and the Au content in this catalyst D-7 were measured to be 0.05 wt. % and 0.02 wt. %, respectively.

Catalyst Application

Figure 5:
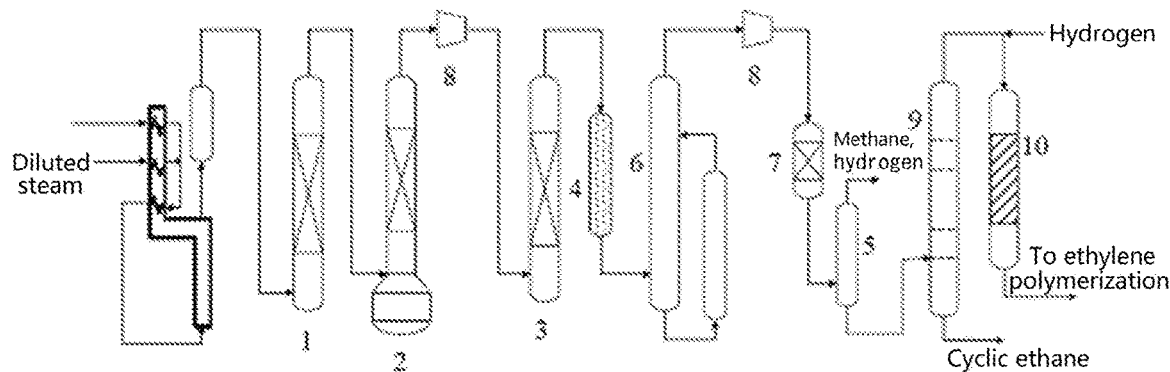
FIG. 5 is a flow chart of an ethylene refining process with a front-end deethanization hydrogenation procedure.

The catalysts prepared in Example 7 and Comparative Example 7 were respectively used in the ethylene refining process with a front-end deethanization hydrogenation process procedure. The process flow chart is shown in FIG. 5. The C2 fraction obtained by steam cracking of petroleum hydrocarbon is treated by sequentially passing through an oil washing tower 1, a water washing tower 2, an alkaline washing tower 3, a dryer 4 and a deethanizer 6 and then entered a C2 hydrogenation reactor 7 for selective hydrogenation to remove traces of acetylene, and then treated by sequentially passing through a demethanizer 5, an ethylene refining column 9 and an ethylene refining reactor 10, wherein compressors 8 were provided between the water washing tower 2 and the alkaline washing tower 3 and between the deethanizer 6 and the C2 hydrogenation reactor 7.

The reaction was carried out with one C2 hydrogenation reactor. The reactor has a gas dispensing system and is a fixed-bed adiabatic reactor.

The content of $C_2H_2$ in the reaction material entering the C2 hydrogenation reactor was 15 µL/L.

Reaction conditions: the space velocity of the material gas is 8000 $h^{-1}$, the reaction pressure is 1.8 MPa, the catalyst loading for the reactor is 500 mL, and the $H_2/C_2H_2$ in the reactor=5:1 (molar ratio). The results of the reaction for 500 hours are shown in Table 10.

TABLE 10

| Catalyst | Reactor inlet temperature (° C.) | Temperature rise (° C.) | $C_2H_2$ residual amount (µL/L) | Ethylene selectivity (%) | Green oil amount (g) |
|---|---|---|---|---|---|
| S-7 | 30 | 14 | 0 | 80 | 1.5 |
| D-7 | 30 | 13 | 1.3 | 33 | 5.8 |

EXAMPLE 8

500 g of a cylindrical θ-$Al_2O_3$ carrier having Φ4.5 mm, a height of 4.5 mm, a specific surface area of 50.0 $m^2$/g, a pore volume of 0.31 mL/g and a bulk density of 0.73 g/$cm^3$ was weighed. The carrier after modification with alkaline earth element Mg has a Mg content of 0.15 wt. %. The pore size of the carrier is 20-220 nm.

130.79 g of 4,4'-dihydroxy-2,2'-bipyridine was dissolved in 650 mL of ethanol to obtain a solution. The above carrier was impregnated in this solution and allowed to stand for 8 hours, to allow 4,4'-dihydroxy-2,2'-bipyridine in the solution to be fully supported on the carrier. Then the solid reaction product was dried at 90° C. for 8 hours, to obtain a hydroxy-bipyridine/$Al_2O_3$ precursor.

1.03 g of Pd(NO$_3$)$_2$ and 6.94 g of Ni(NO$_3$)$_2$.6H$_2$O were dissolved in 500 mL of deionized water and the pH was adjusted to 2.5 with an appropriate amount of nitric acid to obtain a mixed solution. The above hydroxy-bipyridine/$Al_2O_3$ precursor was added into the mixed solution, stirred for 1 hour and allowed to stand for 8 hours. The residual liquid was decanted and the solid reaction product was dried at 110° C. for 6 hours, to obtain a (Pd—Ni)-hydroxy-bipyridine/$Al_2O_3$ precursor (wherein the molar ratio of hydroxy-bipyridine to (Pd+Ni) is 25).

The above (Pd—Ni)-hydroxy-bipyridine/$Al_2O_3$ precursor was calcined in an air atmosphere at 500° C. for 4 hours to obtain a (Pd—Ni)/$Al_2O_3$ catalyst.

The above (Pd—Ni)/$Al_2O_3$ catalyst was placed in a fixed-bed reactor, and subjected to a reduction treatment at 120° C. for 3 hours with a hydrogen gas having a purity of 99.9% at a space velocity of 200 $h^{-1}$, to obtain a reduced palladium-based supported hydrogenation catalyst S-8. The Pd content and the Ni content in this catalyst S-8 were measured to be 0.084 wt. % and 0.28 wt. %, respectively.

COMPARATIVE EXAMPLE 8

500 g of a cylindrical θ-$Al_2O_3$ carrier having Φ4.5 mm, a height of 4.5 mm, a specific surface area of 50.0 $m^2$/g, a pore volume of 0.31 mL/g and a bulk density of 0.73 g/$cm^3$ was weighed. The carrier after modification with alkaline earth element Mg has a Mg content of 0.15 wt. %. The pore size of the carrier is 20-220 nm.

2.2 g of polystyrene-acrylonitrile (SAN) was added to 600 mL dimethylformamide (DMF), and stirred at room temperature until the SAN was completely dissolved to obtain a solution. The above carrier was added to the solution, fully stirred and allowed to stand for 1 hour. The solid reaction product was dried at 80° C. for 5 hours, to obtain a SAN/$Al_2O_3$ precursor.

The above SAN/$Al_2O_3$ precursor was added into 1000 mL of deionized water, and 57.6 g of ethylenediamine was added, stirred until the precursor was completely dissolved and reacted under reflux for 4 hours. After cooling to room temperature, the solid reaction product was washed to neutrality with deionized water and then dried at 80° C. for 5 hours, to obtain a functionalized SAN/$Al_2O_3$ precursor.

1.03 g of Pd(NO$_3$)$_2$ and 6.94 g of Ni(NO$_3$)$_2$.6H$_2$O were dissolved in 500 mL of deionized water and the pH was adjusted to 2.5 with an appropriate amount of nitric acid to obtain a mixed solution. The above functionalized SAN/$Al_2O_3$ precursor was added into the mixed solution, and stirred for 5 minutes. The residual liquid was decanted. The solid reaction product was washed to neutrality with deionized water and dried at 100° C. for 3 hours, to obtain a (Pd—Ni)-SAN/$Al_2O_3$ precursor.

The above (Pd—Ni)-SAN/$Al_2O_3$ precursor was calcined in an air atmosphere at 450° C. for 4 hours to obtain a (Pd—Ni)/$Al_2O_3$ catalyst.

The above (Pd—Ni)/$Al_2O_3$ catalyst was placed in a fixed-bed reactor, and subjected to a reduction treatment at 120° C. for 3 hours with a hydrogen gas having a purity of 99.9% at a space velocity of 200 $h^{-1}$, to obtain a reduced palladium-based supported hydrogenation catalyst D-8. The Pd content and the Ni content in this catalyst D-8 were measured to be 0.084 wt. % and 0.28 wt. %, respectively.

Catalyst Application

Figure 6:
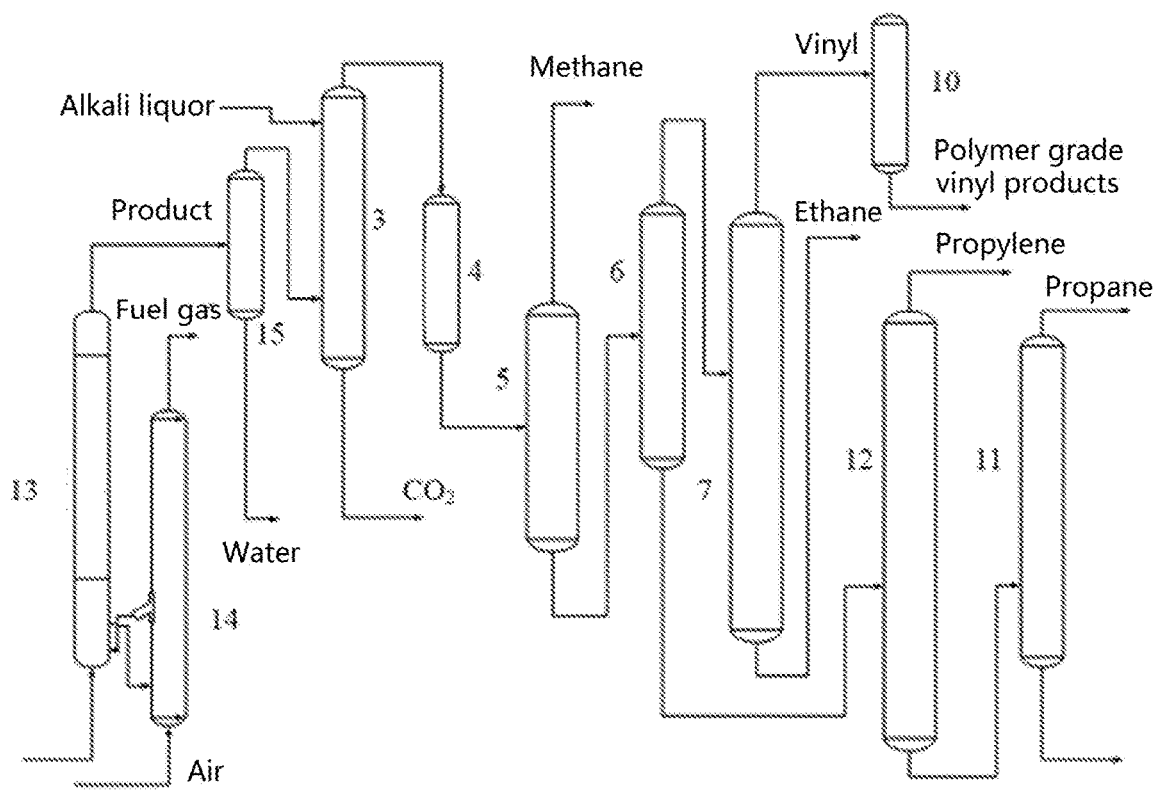
FIG. 6 is a flow chart of a Methanol-to-olefin (MTO) process with a sequential separation procedure.

The catalysts prepared in Example 8 and Comparative Example 8 were respectively used in the Methanol-to-olefin (MTO) process with a sequential separation procedure. The process flow chart is shown in FIG. 6. The product produced by a Methanol-to-ethylene reactor 13 is treated by sequentially passing through an oil washing tower 1, a water washing tower 2, an alkaline washing tower 3, a dryer 4, a demethanizer 5 and a deethanizer 6, and then the overhead product of the deethanizer 6 entered a C2 hydrogenation reactor 7 for selective hydrogenation to remove traces of acetylene, followed by treatment in an ethylene refining reactor 10; the bottom product of the deethanizer 6 is treated by sequentially passing through a propylene refining column 12 and a depropanizer 11; wherein the Methanol-to-ethylene reactor 13 was also connected to a regenerator 14.

The reaction was carried out with one C2 hydrogenation reactor. The reactor has a gas dispensing system and is a fixed-bed adiabatic reactor.

The content of $C_2H_2$ in the reaction material entering the C2 hydrogenation reactor was 10 μL/L.

Reaction conditions: the space velocity of the material gas is 6000 h$^{-1}$, the reaction pressure is 2.0 MPa, the catalyst loading for the reactor is 300 mL, and the $H_2/C_2H_2$ in the reactor=5:1 (molar ratio). The results of the reaction for 500 hours are shown in Table 11.

TABLE 11

| Catalyst | Reactor inlet temperature (° C.) | Temperature rise (° C.) | $C_2H_2$ residual amount (μL/L) | Ethylene selectivity (%) | Green oil amount (g) |
|---|---|---|---|---|---|
| S-8 | 32 | 6 | 0 | 45 | 1.8 |
| D-8 | 32 | 9 | 0.2 | 12 | 2.9 |

EXAMPLE 9

500 g of a cylindrical $Al_2O_3$ carrier of a mixed crystal form of δ and θ, having Φ4.5 mm, a height of 4.5 mm, a specific surface area of 48.0 m$^2$/g, a pore volume of 0.32 mL/g and a bulk density of 0.73 g/cm$^3$ was weighed. The carrier after modification with alkaline metal element Na has a Na content of 0.12 wt. %. The pore size of the carrier exhibits a bimodal pore size distribution with pore sizes of 20-35 nm and 200-450 nm, respectively.

106.52 g of 4,4'-dihydroxy-2,2'-bipyridine was dissolved in 600 mL of ethanol to obtain a solution. The above carrier was impregnated in this solution and allowed to stand for 8 hours, to allow 4,4'-dihydroxy-2,2'-bipyridine in the solution to be fully supported on the carrier, the solid reaction product was dried at 90° C. for 8 hours, to obtain a hydroxy-bipyridine/$Al_2O_3$ precursor.

0.49 g of $Pd(NO_3)_2$ and 1.77 g of $Cu(NO_3)_2$ were dissolved in 600 mL of deionized water and the pH was adjusted to 2.5 with an appropriate amount of nitric acid to obtain a mixed solution. The above hydroxy-bipyridine/$Al_2O_3$ precursor was added into the mixed solution, stirred for 1 hour and allowed to stand for 8 hours. The residual liquid was decanted and the solid reaction product was dried at 100° C. for 8 hours, to obtain a (Pd—Cu)-hydroxy-bipyridine/$Al_2O_3$ precursor (wherein the molar ratio of hydroxy-bipyridine to (Pd+Cu) is 50).

The above (Pd—Cu)-hydroxy-bipyridine/$Al_2O_3$ precursor was calcined in an air atmosphere at 500° C. for 4 hours to obtain a (Pd—Cu)/$Al_2O_3$ catalyst.

The above (Pd—Cu)/$Al_2O_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst S-9. The Pd content and the Cu content in this catalyst S-9 were measured to be 0.04 wt. % and 0.12 wt. %, respectively.

COMPARATIVE EXAMPLE 9

500 g of a cylindrical $Al_2O_3$ carrier of a mixed crystal form of δ and θ, having Φ4.5 mm, a height of 4.5 mm, a specific surface area of 48.0 m$^2$/g, a pore volume of 0.32 mL/g and a bulk density of 0.73 g/cm$^3$ was weighed The carrier after modification with alkaline metal element Na has a Na content of 0.12 wt. %. The pore size of the carrier exhibits a bimodal pore size distribution with pore sizes of 20-35 nm and 200-450 nm, respectively.

2.2 g of polystyrene acrylonitrile (SAN) was added to 600 mL dimethylformamide (DMF), and stirred at room temperature until the SAN was completely dissolved to obtain a solution. The above carrier was added to the solution, fully stirred and allowed to stand for 1 hour. The solid reaction product was dried at 70° C. for 5 hours, to obtain a SAN/$Al_2O_3$ precursor.

The above SAN/$Al_2O_3$ precursor was added into 1000 mL of deionized water, and 57.6 g of ethylenediamine was added, stirred until the precursor was completely dissolved and reacted under reflux for 4 hours. After cooling to room temperature, the solid reaction product was washed to neutrality with deionized water and then dried at 80° C. for 3 hours, to obtain a functionalized SAN/$Al_2O_3$ precursor.

0.49 g of $Pd(NO_3)_2$ and 1.77 g of $Cu(NO_3)_2$ were dissolved in 600 mL of deionized water and the pH was adjusted to 2.5 with an appropriate amount of nitric acid to obtain a mixed solution. The above functionalized SAN/$Al_2O_3$ precursor was added into the mixed solution and stirred for 5 minutes. The residual liquid was decanted. The solid reaction product was washed to neutrality with deionized water, and then dried at 120° C. for 5 hours, to obtain a (Pd—Cu)-SAN/$Al_2O_3$ precursor.

The above (Pd—Cu)-SAN/$Al_2O_3$ precursor was calcined in an air atmosphere at 500° C. for 4 hours to obtain a (Pd—Cu)/$Al_2O_3$ catalyst.

The above (Pd—Cu)/$Al_2O_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst D-9. The Pd content and the Cu content in this catalyst D-9 were measured to be 0.04 wt. % and 0.12 wt. %, respectively.

Catalyst Application

Figure 7:
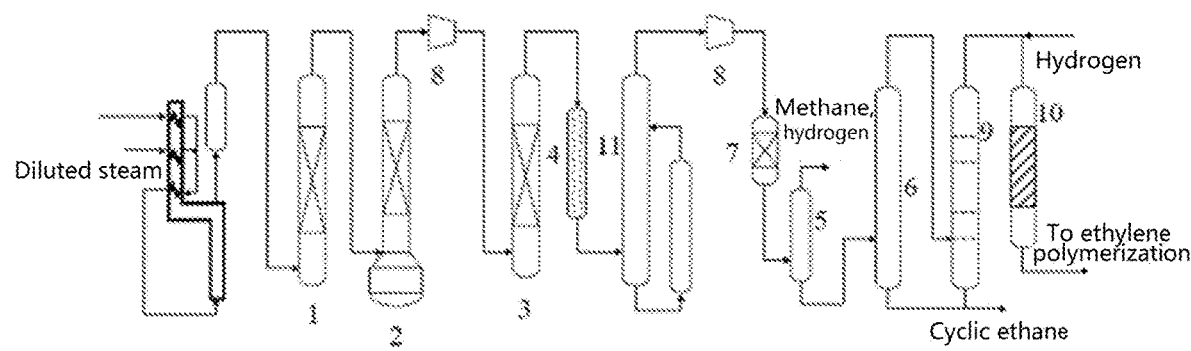
FIG. 7 is a flow chart of an ethylene refining process with a front-end depropanization hydrogenation procedure.

The catalysts prepared in Example 9 and Comparative Example 9 were respectively used in the ethylene refining process with a front-end depropanization hydrogenation procedure. The process flow chart is shown in FIG. 7. The C2 fraction obtained by steam cracking of petroleum hydrocarbon is treated by sequentially passing through an oil washing tower 1, a water washing tower 2, an alkaline washing tower 3, a dryer 4 and a depropanizer 11, and then entered a C2 hydrogenation reactor 7 for selective hydrogenation to remove traces of acetylene, and then treated by sequentially passing through a demethanizer 5, a deethanizer 6, an ethylene refining column 9 and an ethylene refining reactor 10, wherein compressors 8 were provided between the water washing tower 2 and the alkaline washing tower 3 and between the depropanizer 11 and the C2 hydrogenation reactor 7.

The reaction was carried out with one C2 hydrogenation reactor. The reactor has a gas dispensing system and is a fixed-bed adiabatic reactor.

The content of $C_2H_2$ in the reaction material entering the C2 hydrogenation reactor was 12 μL/L.

Reaction conditions: the space velocity of the material gas is 20000 h$^{-1}$, the reaction pressure is 2.0 MPa, the catalyst loading for the reactor is 500 mL, and the $H_2/C_2H_2$ in the reactor=5.6:1 (molar ratio). The results of the reaction for 1000 hours are shown in Table 12.

TABLE 12

| Catalyst | Reactor inlet temperature (° C.) | Temperature rise (° C.) | $C_2H_2$ residual amount (μL/L) | Ethylene selectivity (%) | Green oil amount (g) |
|---|---|---|---|---|---|
| S-9 | 32 | 11 | 0 | 69 | 0.8 |
| D-9 | 32 | 12 | 0.5 | 17 | 2.7 |

EXAMPLE 10

500 g of a spherical α-$Al_2O_3$ carrier having Φ4.0 mm, a specific surface area of 20.0 m²/g, a pore volume of 0.52 mL/g and a bulk density of 0.85 g/cm³ was weighed. The pore size of the carrier is 80-350 nm.

69.5 g of 6,6'-dihydroxy-3,3'-bipyridine was dissolved in 700 mL of ethanol to obtain a solution. The above carrier was impregnated in this solution and allowed to stand for 2 hours, to allow 6,6'-dihydroxy-3,3'-bipyridine to be fully supported on the carrier. Then the solid reaction product was dried at 60° C. for 10 hours, to obtain a hydroxy-bipyridine/$Al_2O_3$ precursor.

0.49 g of $Pd(NO_3)_2$ and 1.82 g of $Pb(NO_3)_2$ were dissolved in 600 mL of deionized water and the pH was adjusted to 2.7 with an appropriate amount of nitric acid to obtain a mixed solution. The above hydroxy-bipyridine/$Al_2O_3$ precursor was added into the mixed solution, stirred for 10 minutes and allowed to stand for 2 hours. The residual liquid was decanted and the solid reaction product was dried at 120° C. for 4 hours, to obtain a (Pd—Pb)-hydroxy-bipyridine/$Al_2O_3$ precursor (wherein the molar ratio of hydroxy-bipyridine to (Pd+Pb) is 20).

The above (Pd—Pb)-hydroxy-bipyridine/$Al_2O_3$ precursor was calcined in an air atmosphere at 550° C. for 2 hours to obtain a (Pd—Pb)/$Al_2O_3$ catalyst.

The above (Pd—Pb)/$Al_2O_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst S-10. The Pd content and the Pb content in this catalyst S-10 were measured to be 0.04 wt. % and 0.23 wt. %, respectively.

COMPARATIVE EXAMPLE 10

500 g of a spherical α-$Al_2O_3$ carrier having Φ4.0 mm, a specific surface area of 20.0 m²/g, a pore volume of 0.52 mL/g and a bulk density of 0.85 g/cm³ was weighed. The pore size of the carrier is 80-350 nm.

8.9 g of polyvinyl chloride (PVC) was dissolved in 800 mL of tetrahydrofuran (THF) to obtain a solution. The above carrier was impregnated in the solution and allowed to stand for 2 hours to allow the PVC in the solution to adsorb onto the carrier surface. The solid reaction product was dried at 100° C. for 3 hours, to obtain a PVC/$Al_2O_3$ precursor.

119.28 g of dicyandiamide and 4.0 g of $Na_2CO_3$ were heated and dissolved in 1000 mL of deionized water, and then the above PVC/$Al_2O_3$ precursor was added and reacted under reflux for 1 hour. After cooling to room temperature, the solid reaction product was washed to neutrality with deionized water and then dried at 60° C. for 10 hours, to obtain a functionalized PVC/$Al_2O_3$ precursor.

0.49 g of $Pd(NO_3)_2$ and 1.82 g of $Pb(NO_3)_2$ were dissolved in 600 mL of deionized water and the pH was adjusted to 2.5 with an appropriate amount of nitric acid to obtain a mixed solution. The above functionalized PVC/$Al_2O_3$ precursor was added into the mixed solution and stirred for 0.5 hours. The residual liquid was decanted. The solid reaction product was washed to neutrality with deionized water and then dried at 120° C. for 4 hours, to obtain a (Pd—Pb)-PVC/$Al_2O_3$ precursor.

The above (Pd—Pb)-PVC/$Al_2O_3$ precursor was calcined in an air atmosphere at 550° C. for 2 hours to obtain a (Pd—Pb)/$Al_2O_3$ catalyst.

The above (Pd—Pb)/$Al_2O_3$ catalyst was placed in a fixed-bed reactor, and subjected to a reduction treatment at 120° C. for 3 hours with a hydrogen gas having a purity of 99.9% at a space velocity of 200 h$^{-1}$, to obtain a reduced palladium-based supported hydrogenation catalyst D-10. The Pd content and the Pb content in this catalyst D-10 were measured to be 0.04 wt. % and 0.23 wt. %, respectively.

Catalyst Application

Figure 8:
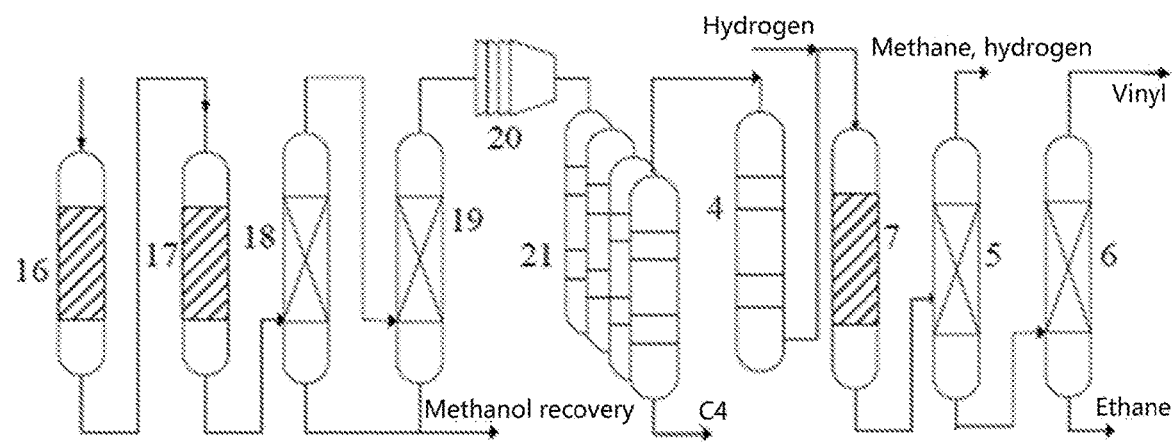
FIG. 8 is a flow chart of a Methanol-to-olefin (MTO) process with a front-end depropanization hydrogenation procedure.

The catalysts prepared in Example 10 and Comparative Example 10 were respectively used in the Methanol-to-olefin (MTO) process with a front-end depropanization hydrogenation procedure. The process flow chart is shown in FIG. 8. Methanol was treated by sequentially passing through a reactor 16 for dehydration of methanol to dimethyl ether (i.e., DME reactor), a methanol-to-propylene reactor (i.e., MTP reactor) 17, a pre-quench separator 18, a quench separator 19, a four-level compressor 20, a four-level separator 21 and a dryer 4, and then entered a C2 hydrogenation reactor 7 for selective hydrogenation to remove traces of acetylene, followed by treatment in a demethanizer 5 and a deethanizer 6 sequentially.

The reaction was carried out with one C2 hydrogenation reactor. The reactor has a gas dispensing system and is a fixed-bed adiabatic reactor.

The content of $C_2H_2$ in the reaction material entering the C2 hydrogenation reactor was 5.3 μL/L.

Reaction conditions: the space velocity of the material gas is 2700 h$^{-1}$, the reaction pressure is 2.0 MPa, the catalyst loading for the reactor is 500 mL, and the $H_2/C_2H_2$ in the reactor=5:1 (molar ratio). The results of the reaction for 1000 hours are shown in Table 13.

TABLE 13

| Catalyst | Reactor inlet temperature (° C.) | Temperature rise (° C.) | $C_2H_2$ residual amount (μL/L) | Ethylene selectivity (%) | Green oil amount (g) |
|---|---|---|---|---|---|
| S-10 | 32 | 7 | 0 | 44 | 1.5 |
| D-10 | 32 | 8 | 1.0 | 24 | 2.7 |

EXAMPLE 11

500 g of a cylindrical $Al_2O_3$ carrier having Φ4.5 mm, a height of 4.5 mm, a specific surface area of 10.0 m²/g, a pore volume of 0.21 mL/g and a bulk density of 0.75 g/cm³ was weighed, and it contained 487.5 g of $Al_2O_3$ and 12.5 g of magnesium oxide, wherein $Al_2O_3$ was in a mixed crystal form of θ and α. The pore size of the carrier exhibits a bimodal pore size distribution with pore sizes of 100-180 nm and 350-750 nm, respectively.

47.2 g of 6,6'-dihydroxy-3,3'-bipyridine was dissolved in 600 mL of ethanol to obtain a solution. The above carrier was impregnated in this solution and allowed to stand for 10 hours, to allow 6,6'-dihydroxy-3,3'-bipyridine to be fully supported on the carrier. Then the solid reaction product was dried at 100° C. for 6 hours, to obtain a hydroxy-bipyridine/$Al_2O_3$ precursor.

0.37 g of $Pd(NO_3)_2$ and 1.18 g of $AgNO_3$ were dissolved in 450 mL of deionized water and the pH was adjusted to 2.5 with an appropriate amount of nitric acid to obtain a mixed solution. The above hydroxy-bipyridine/$Al_2O_3$ precursor was added into the mixed solution, stirred for 1 hour and allowed to stand for 10 hours. The residual liquid was decanted and the solid reaction product was dried at 90° C. for 10 hours, to obtain a (Pd—Ag)-hydroxy-bipyridine/$Al_2O_3$ precursor (wherein the molar ratio of hydroxy-bipyridine to (Pd+Ag) is 30).

The above (Pd—Ag)-hydroxy-bipyridine/$Al_2O_3$ precursor was calcined in an air atmosphere at 600° C. for 2 hours to obtain a (Pd—Ag)/$Al_2O_3$ catalyst.

The above (Pd—Ag)/$Al_2O_3$ catalyst was placed in a fixed-bed reactor, and subjected to a reduction treatment at 100° C. for 4 hours with a hydrogen gas having a purity of 99.9% at a space velocity of 300 $h^{-1}$, to obtain a reduced palladium-based supported hydrogenation catalyst S–11. The Pd content and the Ag content in this catalyst S–11 were measured to be 0.03 wt. % and 0.15 wt. %, respectively.

COMPARATIVE EXAMPLE 11

500 g of a cylindrical $Al_2O_3$ carrier having Φ4.5 mm, a height of 4.5 mm, a specific surface area of 10.0 m²/g, a pore volume of 0.21 mL/g and a bulk density of 0.75 g/cm³ was weighed, and it contained 487.5 g of $Al_2O_3$ and 12.5 g of magnesium oxide, wherein $Al_2O_3$ was in a mixed crystal form of θ and α. The pore size of the carrier exhibits a bimodal pore size distribution with pore sizes of 100-180 nm and 350-750 nm, respectively.

0.37 g of $Pd(NO_3)_2$ and 1.18 g of $AgNO_3$ were dissolved in 450 mL of deionized water and the pH was adjusted to 2.5 with an appropriate amount of nitric acid to obtain a mixed solution. The mixed solution was sprayed onto the above carrier and then shaken for 0.5 hour. The residual liquid was decanted. The solid reaction product was dried at 90° C. for 10 hours and then calcined in an air atmosphere at 600° C. for 2 hours to obtain a (Pd—Ag)/$Al_2O_3$ catalyst.

The above (Pd—Ag)/$Al_2O_3$ catalyst was placed in a fixed-bed reactor, and subjected to a reduction treatment at 100° C. for 4 hours with a hydrogen gas having a purity of 99.9% at a space velocity of 300 $h^{-1}$, to obtain a reduced palladium-based supported hydrogenation catalyst D–11. The Pd content and the Ag content in this catalyst D–11 were measured to be 0.03 wt. % and 0.15 wt. %, respectively.

Catalyst Application

The catalysts prepared in Example 11 and Comparative Example 11 were respectively used in the front-end depropanization hydrogenation process of C2 fraction. The process flow chart is shown in FIG. 3.

The reaction was carried out with three C2 hydrogenation reactors in series, i.e., the outlet material of the first section reactor entered the second section reactor and the outlet material of the second section reactor entered the third section reactor. Each reactor has an independent gas dispensing system, and these reactors are each fixed-bed adiabatic reactors.

The reaction materials come from the top of the depropanizer and the composition thereof is shown in Table 14.

Reaction conditions: the space velocity of the material gas is 10000 $h^{-1}$, the reaction pressure is 3.9 MPa, and the catalyst loading for the three reactors is 500 mL. The results of the reaction for 1000 hours are shown in Table 15.

TABLE 14

| | $H_2$ | $C_2H_2$ | $C_2H_4$ | $C_2H_6$ | $CH_4$ | $C_3H_6$ | $C_3H_8$ | PDMA | CO | $C_4+$ |
|---|---|---|---|---|---|---|---|---|---|---|
| Content (v/v %) | 16.0 | 0.9 | 39.0 | 9.5 | 19.5 | 12 | 2.0 | 0.7 | 0.1 | 0.3 |

TABLE 15

| Catalyst | Reactor section | Inlet temperature (° C.) | Temperature rise (° C.) | $C_2H_2$ residual amount (v/v %) | Ethylene selectivity (%) | Green oil amount (wt. %) |
|---|---|---|---|---|---|---|
| S-11 | First section | 78 | 17 | 0.49 | 87 | 3.5 |
| | Second section | 86 | 14 | 0.18 | 76 | 2.6 |
| | Third section | 93 | 7 | 0 | 63 | 1.4 |
| D-11 | First section | 78 | 20 | 0.68 | 49 | 4.0 |
| | Second section | 86 | 16 | 0.47 | 40 | 3.2 |
| | Third section | 93 | 10 | 0.18 | 32 | 2.9 |

EXAMPLE 12

500 g of a cylindrical carrier containing 481.5 g of α-$Al_2O_3$, 12.5 g of magnesium oxide and 6 g of calcium oxide, having Φ4.5 mm, a height of 4.5 mm, a specific surface area of 8.0 $m^2$/g, a pore volume of 0.38 mL/g and a bulk density of 0.75 g/$cm^3$ was weighed The pore size of the carrier exhibits a bimodal pore size distribution with pore sizes of 100-180 nm and 350-750 nm, respectively.

16.68 g of 6,6'-dihydroxy-3,3'-bipyridine was dissolved in 650 mL of ethanol to obtain a solution. The above carrier was impregnated in this solution and allowed to stand for 12 hours, to allow 6,6'-dihydroxy-3,3'-bipyridine in the solution to be fully supported on the carrier, the solid reaction product was dried at 120° C. for 4 hours, to obtain a hydroxy-bipyridine/$Al_2O_3$ precursor.

0.49 g of Pd($NO_3$)$_2$ and 0.83 g of Cu($NO_3$)$_2$ were dissolved in 600 mL of deionized water and the pH was adjusted to 2.5 with an appropriate amount of nitric acid to obtain a mixed solution. The above hydroxy-bipyridine/$Al_2O_3$ precursor was added into the mixed solution, stirred for 1 hour and allowed to stand for 12 hours. The residual liquid was decanted and the solid reaction product was dried at 120° C. for 4 hours, to obtain a (Pd—Cu)-hydroxy-bipyridine/$Al_2O_3$ precursor (wherein the molar ratio of hydroxy-bipyridine to (Pd+Cu) is 15).

The above (Pd—Cu)-hydroxy-bipyridine/$Al_2O_3$ precursor was calcined in an air atmosphere at 450° C. for 8 hours to obtain a (Pd—Cu)/$Al_2O_3$ catalyst S–12. The Pd content and the Cu content in this catalyst S–12 were measured to be 0.04 wt. % and 0.056 wt. %, respectively.

COMPARATIVE EXAMPLE 12

500 g of a cylindrical carrier containing 481.5 g of α-$Al_2O_3$, 12.5 g of magnesium oxide and 6 g of calcium oxide, having Φ4.5 mm, a height of 4.5 mm, a specific surface area of 8.0 $m^2$/g, a pore volume of 0.38 mL/g and a bulk density of 0.75 g/$cm^3$ was weighed. The pore size of the carrier exhibits a bimodal pore size distribution with pore sizes of 100-180 nm and 350-750 nm, respectively.

6.0 g of dodecylpyridine hydrochloride was dissolved in 600 mL of ethanol to obtain a solution. The above carrier was impregnated in this solution and allowed to stand at room temperature for 48 hours. The solid reaction product was dried at 120° C. for 4 hours to obtain a $Al_2O_3$ precursor containing $C_{12}H_{25}C_5H_4N.HCl$.

0.49 g of Pd($NO_3$)$_2$ and 0.83 g of Cu($NO_3$)$_2$ were dissolved in 600 mL of deionized water and the pH was adjusted to 2.5 with an appropriate amount of nitric acid to obtain a mixed solution. The above $Al_2O_3$ precursor containing $C_{12}H_{25}C_5H_4N.HCl$ was added into the mixed solution and allowed to stand for 2 hours. The residual liquid was decanted and the solid reaction product was dried at 120° C. for 4 hours, to obtain a (Pd—Cu)-alkylpyridine hydrochloride/$Al_2O_3$ precursor.

The above (Pd—Cu)-alkylpyridine hydrochloride/$Al_2O_3$ precursor was calcined in an air atmosphere at 500° C. for 2 hours to obtain a (Pd—Cu)/$Al_2O_3$ catalyst D–12. The Pd content and the Cu content in this catalyst D–12 were measured to be 0.04 wt. % and 0.056 wt. %, respectively.

Catalyst Application

The catalysts prepared in Example 12 and Comparative Example 12 were respectively used in the front-end deethanization hydrogenation process of C2 fraction. The process flow chart is shown in FIG. 2.

The reaction was carried out with one C2 hydrogenation reactor. The reactor has a gas dispensing system and is a fixed-bed adiabatic reactor.

The reaction materials come from the top of the deethanizer and the composition thereof is shown in Table 16.

Reaction conditions: the space velocity of the material gas is 12000 $h^{-1}$, the reaction pressure is 3.6 MPa, and the catalyst loading for the reactor is 500 mL. The results of the reaction for 1000 hours are shown in Table 17.

TABLE 16

|  | $H_2$ | $C_2H_2$ | $C_2H_4$ | $C_2H_6$ | $CH_4$ | CO | $C_4$+ |
|---|---|---|---|---|---|---|---|
| Content (v/v %) | 30 | 0.6 | 33.2 | 5.88 | 30 | 0.008 | 0.312 |

TABLE 17

| Catalyst | Reactor inlet temperature (° C.) | Temperature rise (° C.) | $C_2H_2$ residual amount (µL/L) | Ethylene selectivity (%) | Green oil amount (wt. %) |
|---|---|---|---|---|---|
| S-12 | 85 | 32 | 0.5 | 60 | 1.9 |
| D-12 | 85 | 34 | 475 | 28.6 | 15.6 |

It can be seen from the above Examples and Comparative Examples that as compared with the catalyst prepared by the conventional impregnation method, the catalyst prepared by using a carrier comprising chlorine-containing organics and the catalyst prepared by grafting the functional group with an organic polymer compound and being supported on a carrier, when the content of the active components is the same, all the catalysts prepared by the method of the present invention exhibit more excellent activity, selectivity and anti-coking performance when used in various selective hydrogenation processes of acetylene, and the amount of green oil generated during the hydrogenation is also greatly reduced. Meanwhile, the reduction in the amount of the green oil production reduces the coverage of active centers of the catalyst by the by-products, the activity and selectivity of the catalyst are well maintained, and the service life of the catalyst is extended.

The invention claimed is:

1. A method of preparing a palladium-based supported hydrogenation catalyst, comprising:
    impregnating an $Al_2O_3$-containing carrier with an organic solution containing a bipyridine compound;
    optionally drying followed by impregnating with a mixed solution containing palladium ions and M metal cations, wherein the M metal cations is selected from one of Ag, Au, Ni, Pb or Cu; and
    optionally drying, and calcining to obtain the palladium-based supported hydrogenation catalyst;
    wherein, the bipyridine compound is 4,4'-dihydroxy-2,2'-bipyridine and/or 6,6'-dihydroxy-3,3'-bipyridine.

2. The method according to claim 1, wherein the impregnation of the $Al_2O_3$-containing carrier with the organic solution containing the bipyridine compound is carried out at 20-60° C., and the impregnation duration is 2 to 24 hours.

3. The method according to claim 1, wherein the impregnation of the bipyridine compound impregnated $Al_2O_3$ precursor with the mixed solution is carried out at 30-100° C., and the impregnation duration is 2 to 24 hours.

4. The method according to claim 1, wherein the calcination temperature is 300-600° C., and the duration is 2 to 12 hours.

5. The method according to claim 1, wherein the $Al_2O_3$-containing carrier comprises alumina and/or a mixture containing alumina and an additional oxide, wherein the additional oxide includes a combination of one or more of silica, titania, magnesium oxide and calcium oxide.

6. The method according to claim 1, wherein a crystal form of $Al_2O_3$ in the $Al_2O_3$-containing carrier is γ, δ, θ, α, or a mixed crystal form of some of these crystal forms.

7. The method according to claim 1, wherein the $Al_2O_3$-containing carrier is in the form of spherical, tooth-spherical, cylindrical, ring, bar, three-leaf clover or four-leaf clover shape.

8. The method according to claim 1, wherein the molar ratio of the palladium ions to the M metal cations in the mixed solution is 1-100:1.

9. The method according to claim 1, wherein in the mixed solution, when M is Ag, the molar ratio of Ag to Pd is 0.4-10:1; when M is Au, the molar ratio of Au to Pd is 0.5-15:1; when M is Ni, the molar ratio of Ni to Pd is 0.4-20:1; when M is Pb, the molar ratio of Pb to Pd is 1-10:1; when M is Cu, the molar ratio of Cu to Pd is 1-10:1.

10. The method according to claim 1, wherein the pH of the mixed solution is 1.5-4.0.

11. The method according to claim 1, further comprising subjecting the palladium-based supported hydrogenation catalyst to a reduction treatment with a hydrogen-containing gas before use thereof, to obtain the reduced palladium-based supported hydrogenation catalyst.

* * * * *